United States Patent
Wu et al.

(10) Patent No.: US 10,690,675 B2
(45) Date of Patent: Jun. 23, 2020

(54) METHODS FOR ENRICHING GLYCOPEPTIDES FOR GLOBAL ANALYSIS OF GLYCOPROTEINS

(71) Applicant: Georgia Tech Research Corporation, Atlanta, GA (US)

(72) Inventors: Ronghu Wu, Atlanta, GA (US); Weixuan Chen, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 15/952,946

(22) Filed: Apr. 13, 2018

(65) Prior Publication Data

US 2018/0299462 A1    Oct. 18, 2018

Related U.S. Application Data

(60) Provisional application No. 62/485,588, filed on Apr. 14, 2017.

(51) Int. Cl.
*G01N 33/68* (2006.01)
*G01N 1/40* (2006.01)
*C07F 5/02* (2006.01)

(52) U.S. Cl.
CPC ......... *G01N 33/6842* (2013.01); *C07F 5/025* (2013.01); *G01N 1/405* (2013.01); *G01N 33/6848* (2013.01); *G01N 2440/38* (2013.01); *G01N 2570/00* (2013.01)

(58) Field of Classification Search
CPC .............. G01N 33/6842; G01N 1/405; G01N 33/6848; G01N 2440/38; G01N 2570/00
USPC ....................................................... 536/124
See application file for complete search history.

(56) References Cited

U.S. PATENT DOCUMENTS

2008/0200434 A1* 8/2008 Daniloff ................. A61K 31/69
514/64

OTHER PUBLICATIONS

Griffin et al. Solvent extraction and purification of sugars from hemicellulose hydrolysates using boronic acid carriers. J Chem Technol Biotechnol 79:505-511 (online: 2004). (Year: 2004).*
James et al. A saccharide 'sponge'. Synthesis and properties of a dendritic boronic acid. Chem. Commun., 6:705-706, 1996. (Year: 1996).*
Pal A. A thesis: Design, Synthesis, and Screening of a Library of Peptidyl Bis-Boroxoles as Low Molecular Weight Receptors for Complex Oligosaccharides in Neutral Water: Identification of a Selective Receptor for the Tumour Marker TF-Antigen, U of Alberta, Fall 2009, Edmonton, Alberta, pp. 1-135. (Year: 2009).*

* cited by examiner

*Primary Examiner* — Yih-Horng Shiao
(74) *Attorney, Agent, or Firm* — Troutman Sanders LLP; Ryan A. Schneider; Chris N. Davis

(57) ABSTRACT

Compositions and methods for enriching glycocompounds are disclosed which can comprise a glycocompound bound to a boronic acid compound which can be conjugated to a dendrimer.

10 Claims, 25 Drawing Sheets

1,044 N-glycosylation sites

1,302 N-glycoproteins

4195 protein N-glycosylation sites 1608 glycoproteins

TNFRSF8 (CD30)

CD96

METHODS FOR ENRICHING GLYCOPEPTIDES FOR GLOBAL ANALYSIS OF GLYCOPROTEINS

CROSS-REFERENCE TO RELATED APPLICATIONS

This application, filed Apr. 13, 2018, claims the benefit of U.S. Provisional Patent Application No. 62/485,588, filed Apr. 14, 2017, entitled "New Technology to Efficiently Enrich Glycopeptides for Global Analysis of Glycoproteins," the entire contents and substance of which are hereby incorporated by reference as if fully set forth below.

STATEMENT OF FEDERALLY SPONSORED RESEARCH

This invention was made with U.S. Government support under Contract No. 1454501 awarded by the National Science Foundation (NSF). The U.S. Government has certain rights in the invention.

BACKGROUND

Protein glycosylation is ubiquitous in biological systems and essential for cell survival. However, the heterogeneity of glycans and low abundance of many glycoproteins complicate their global analysis. Glycosylation is one of the most common and essential protein modifications in cells. It often determines protein folding, trafficking and stability, and regulates many cellular events, especially cell-cell communication, cell-matrix interactions, and cellular response to environmental cues. Glycoproteins contain a wealth of information related to cellular developmental and diseased statuses, and aberrant protein glycosylation is directly related to human disease, including cancer and infectious diseases. Global analysis of protein glycosylation is critical in understanding glycoprotein functions and identifying glycoproteins as biomarkers and drug targets. However, due to the low abundance of many glycoproteins and heterogeneity of glycans, it is extraordinarily challenging to comprehensively analyze glycoproteins in complex biological samples.

Currently mass spectrometry (MS)-based proteomics provides a unique opportunity to globally analyze protein modifications, including glycosylation. However, effective enrichment prior to MS analysis is imperative for each type of protein modification. For example, with the maturity of phosphoprotein enrichment methods, the global analysis of protein phosphorylation has advanced tremendously, from the identification of several hundred phosphorylation sites a decade ago to over ten thousand sites in recent studies.

In order to comprehensively analyze protein glycosylation in complex biological samples, several glycoprotein/glycopeptide enrichment methods have been reported, including lectin-based and hydrazide chemistry-based methods, and hydrophilic interaction liquid chromatography (HILIC). Currently lectin-based methods are most commonly used to enrich glycopeptides prior to MS analysis. Due to the inherent specificity of lectins, each type of lectin can only recognize a specific glycan structure, and thus, no single lectin or a combination of several lectins can universally enrich all glycosylated peptides or proteins. HILIC has also been extensively used to enrich glycopeptides based on their increased hydrophilicity by glycans. However, this method lacks specificity because it cannot distinguish glycopeptides from many hydrophilic non-glycopeptides. Additionally, two methods, isotope-targeted glycoproteomics (IsoTaG) and solid phase extraction of N-linked glycans and glycosite-containing peptides (NGAG), have been reported. By using IsoTaG, several N-glycopeptides and intact and fully elaborated O-glycopeptides from several proteins across three human cell lines were identified. NGAG was designed for N-glycopeptide enrichment, and several unique N-glycopeptides were identified in mammalian cells. According to prediction and computational results, protein glycosylation is the most common modification. Despite the considerable progress that has been made in the past decade, there is still a substantial gap between the number of glycoproteins reported in the literature and those existing in complex biological samples. Effective enrichment of glycopeptides/glycoproteins will profoundly advance the global analysis of protein glycosylation through MS-based proteomics.

Previously, boronic acid (BA) was demonstrated to have potential in enriching glycopeptides for the global analysis of protein glycosylation because of its reversible covalent interactions with glycans. However, the method suffers from relatively weak interactions; therefore, low-abundance glycoproteins are not effectively enriched. Accordingly, methods and compositions for enriching glycoproteins are needed that overcome the problems of the low abundance of many glycoproteins and heterogeneity of glycans.

SUMMARY

Some embodiments of the present disclosure can be a method for enriching a glycocompound, the glycocompound can comprise a glycan component and the method can comprise: contacting the glycocompound with a boronic acid compound to form a glycocompound-boronic acid complex, wherein the glycocompound can be reversibly bound to the boronic acid compound. In some embodiments, the boronic acid compound can be a compound of Formula I:

Formula I wherein: $R_1$ can be selected from unsubstituted or substituted alkyl, unsubstituted or substituted heteroalkyl, unsubstituted or substituted aryl, and unsubstituted or substituted heteroaryl; and $R_2$ can be selected from H, a substituted or unsubstituted $C_1$-$C_6$ alkyl, and a $C_1$-$C_3$ alkylene, which together with $R_1$ can form a five- to seven-membered ring.

Some embodiments of the present disclosure can be a composition comprising: a dendrimer-boronic acid (DBA) complex; and a glycocompound reversibly bound to the DBA complex to form a glycocompound-DBA complex. In some embodiments, the DBA complex can comprise a boronic acid compound of Formula I conjugated to a dendrimer, wherein Formula I can be:

Formula I wherein: $R_1$ can be selected from unsubstituted or substituted alkyl, unsubstituted or substituted heteroalkyl, unsubstituted or substituted aryl, and unsubstituted or substituted heteroaryl; and $R_2$ can be selected from H, a substituted or unsubstituted $C_1$-$C_6$ alkyl, and a $C_1$-$C_3$ alkylene, which together with $R_1$ can form a five- to seven-membered ring.

Some embodiments of the present disclosure can be a method for analyzing glycosylation sites on a glycocompound, the glycocompound can comprise at least one glycan component, the method can comprise: contacting the glycocompound with a dendrimer-boronic acid (DBA) complex to form a glycocompound-(DBA) complex; washing the glycocompound-DBA complex to remove non-glycocompounds from the glycocompound-DBA complex; releasing the glycocompound from the DBA complex to form an enriched glycocompound; cleaving the at least one glycan component from the enriched glycocompound; and analyzing the at least one glycan component.

BRIEF DESCRIPTION OF THE DRAWINGS

(FIG. 1a) Structures of boronic acid derivatives tested in this work. (FIG. 1b) The number of glycopeptides identified with each BA derivative at varying pH values from the parallel experiments.

(FIG. 2a) The structure of BA derivative II (benzoboroxole) conjugated dendrimer. (FIG. 2b) An example of the synergistic interactions between multiple benzoboroxole molecules in a dendrimer and several sugars within one glycan of a glycopeptide. (FIG. 2c) The effect of synthesis cycles and corresponding dendrimer size on the enrichment of glycopeptides: total glycopeptides (left bars), unique glycopeptides (middle bars) and glycoproteins (right bars) identified in parallel experiments. (FIG. 2d) The effect of reaction time on the N-glycopeptide identification.

(FIG. 3a) Optimization of the concentrations of TFA as the ion-pairing reagent for ZIC-HILIC enrichment. (FIG. 3b) The numbers of unique glycopeptides (left bars) and glycoproteins (right bars) identified using each of the three methods (Lectin, ZIC-HILIC and DBA) from parallel experiments. (FIG. 3c) Comparison of the enrichment specificity for three enrichment methods. The error bar represents the standard error of the mean calculated from triplicate experiments.

(FIG. 4a) Protein N-glycosylation sites identified in biological duplicate experiments. (FIG. 4b) Abundance distributions of the whole proteome (left bars) and N-glycoproteins identified here (right bars). (FIG. 4c) Distribution of the number of mannose residues per glycan on all identified O-glycopeptides including total O-glycopeptides (left bars) and unique O-glycopeptides (right bars). (FIG. 4d) Percentages of S, T and N in O-glycopeptides (right bars) compared to the whole proteome (left bars). (FIG. 4e) Comparison of O- and N-glycoproteins identified in yeast cells. (FIG. 4f) Clustering of O-glycoproteins based on cellular compartment. P values are calculated by a modified Fisher's exact test.

(FIG. 5a) Comparison of unique protein N-glycosylation sites identified in MCF7 cells in duplicate experiments. (FIG. 5b) Comparison of unique glycosylation sites and glycoproteins identified with the boronic acid derivative magnetic beads (designated as BA, shown in left bars) and with the dendrimer beads conjugated with the boronic acid derivative (DBA) (right bars). (FIG. 5c) Abundance distributions of N-glycoproteins identified with the BA (left bars) or DBA (right bars) beads. (FIG. 5d) Protein clustering results for 180 N-glycoproteins identified exclusively in Jurkat cells. (FIG. 5e) Distribution of membrane proteins (Type I, II, III & IV, and multi-pass transmembrane (TM)) among all identified N-glycoproteins. (FIG. 5f) N-glycosylation site locations on 301 receptors with X-axis as the TM domain. Each glycoprotein sequence was aligned against the transmembrane (TM) domain, and the glycosylation sites are indicated as yellow dots. All sites are located in the extracellular space. (FIG. 5g) Domain analysis of N-glycoproteins showing the number of N-glycoproteins containing the most highly-enriched domains and their corresponding P values.

(FIG. 6a) Comparison of glycoproteins with one HexNAc identified with BA (right bars) and DBA (left bars), which clearly shows that the results from DBA are substantially better. (FIG. 6b) Distribution of O-glycoproteins modified with HexNAc(1) identified in HEK 293T cells based on cellular compartment. (FIG. 6c) Proposed mechanism of the interactions between DBA and GlcNAc benefiting from synergistic interactions. (FIG. 6d) Cellular compartment distributions of glycoproteins containing one HexNAc identified in the three types of human cells (left bars—MCF7, middle bars—Jurkat and right bars—HEK 293T).

(FIG. 17a) AGC target for full MS, (FIG. 17b) AGC target for MS2 (tandem mass spectrum), (FIG. 17c) comparison of Top10 (selection of the 10 most abundant ion species) and Top15 (selection of the 15 most abundant ion species) methods, (FIG. 17d) normalized collision energy, (FIG. 17e) maximum ion accumulation time for MS2. The error bar represents the standard error of the mean calculated from duplicate experiments.

DETAILED DESCRIPTION

Figure 1A:
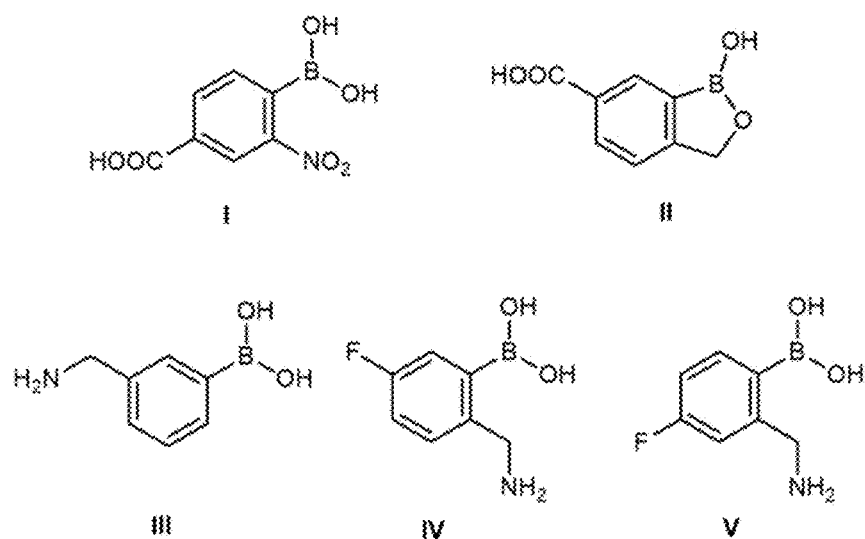
FIG. 1a-1b. Structures of boronic acid derivatives and experimental results using different derivatives.

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Embodiments of the present disclosure include compositions and methods for effectively enriching glycocompounds, including glycopeptides and glycoproteins, that allow global analysis of glycosylation sites on glycocompounds. As used herein, a "glycocompound" is a compound that contains a glycan component which includes one or more hydroxyl groups. A glycocompounds can be for example, a glycoprotein, a glycopeptide, a glycolipid, and the like. In some embodiments, the glycocompound can be a glycopeptide or a glycoprotein. A person of ordinary skill in the art would know that a glycopeptide is a compound in which a glycan (e.g., carbohydrate) component is linked to a peptide component, and that a glycoprotein is a compound in which a glycan (e.g., carbohydrate) component is linked to a protein component.

In some embodiments, the method can comprise contacting the glycocompound with a boronic acid compound to form a glycocompound-boronic acid-complex. As used herein a "boronic acid compound" is a boric-acid derivative compound with a general formula of:

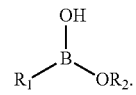

In some embodiments, the glycocompound can be reversibly bound to the boronic acid compound. In some embodiments, the glycocompound can be reversibly covalently bound to the boronic acid compound. In some embodiments, the glycan component of the glycocompound can be reversibly bound to the boronic acid compound. In some embodiments, a hydroxyl moiety, or a plurality of hydroxyl moieties, on the glycan component of the glycocompound can be reversibly bound to the boronic acid compound. In some embodiments, the binding of the glycocompound to the boronic acid compound can be pH dependent. For example, in some embodiments, under basic conditions, the glycocompound can bind to the boronic acid compound to form the glycocompound-boronic acid-complex and under acidic conditions, the glycocompound can be released from the boronic acid compound. One advantage of the reversible nature of the glycocompound-boronic acid-complex formation is that the enriched glycocompound can remain intact after release of the glycocompound from the boronic acid compound, which can allow for site identification, analysis of glycan structures and identification of protein glycosylation. In some embodiments, contacting the glycocompound with the boronic acid compound step can be performed under basic conditions, i.e., at a basic pH. In some embodiments, the contacting step can be at a pH of from about 7 to about 14. In some embodiments, the contacting step can be at a pH of from about 8 to about 14. In some embodiments, the contacting step can be at a pH of about 8, about 9, about 10, about 11, about 12, about 13, or about 14. In some embodiments, the contacting step can be at a pH of about 10. In some embodiments, the contacting step can be at a pH of about 11. In some embodiments, the contacting step can be performed at a pH of from about 10 to about 11.

In some embodiments, the boronic acid compound can be a compound of Formula I:

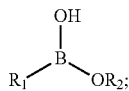

Formula I wherein $R_1$ can be selected from unsubstituted or substituted alkyl, unsubstituted or substituted heteroalkyl, unsubstituted or substituted aryl, and unsubstituted or substituted heteroaryl; and $R_2$ can be selected from H, a substituted or unsubstituted $C_1$-$C_6$ alkyl, and a $C_1$-$C_3$ alkylene, which together with $R_1$ can form a five- to seven-membered ring. In some embodiments, $R_1$ can be an unsubstituted or substituted aryl and $R_2$ can be H. In some embodiments, $R_1$ can be an unsubstituted or substituted aryl and $R_2$ can a methylene, which together with $R_1$ can form a five-membered ring. In some embodiments the compound of Formula I can be:

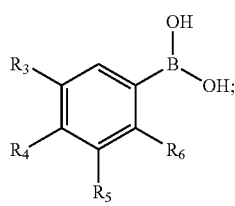

wherein $R_3$, $R_4$, $R_5$, and $R_6$ can be independently selected from H, halogen, —C(=O)—OH, —($C_{1-8}$- alkylenyl)-NH$_2$, and —NO$_2$; and at least one of $R_3$, $R_4$, $R_5$, and $R_6$ is not H. In some embodiments, $R_6$ can be selected from —NO$_2$, and —($C_{1-8}$-alkylenyl)-NH$_2$; and one of $R_3$ and $R_4$ can be independently selected from halogen, —C(=O)—OH, and H. In some embodiments, $R_6$ can be —($C_{1-8}$-alkylenyl)-NH$_2$; one of $R_3$ and $R_4$ can be halogen; and $R_5$ can be H. In some embodiments, $R_6$ can be —CH$_2$—NH$_2$; $R_3$ can be H; $R_4$ can be F and $R_5$ can be H. In some embodiments, $R_6$ can be —CH$_2$—NH$_2$; and one of $R_3$ can be F; $R_4$ can be H and $R_5$ can be H. In some embodiments, $R_3$ can be —CH$_2$—NH$_2$, and $R_4$, $R_5$, and $R_6$ can each be H. In some embodiments, the compound of Formula I can be:

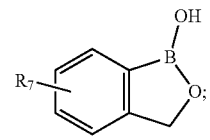

wherein $R_7$ is selected from C(=O)—OH, or —CH$_2$—NH$_2$. In some embodiments, the compound of Formula I can be

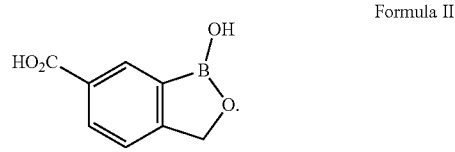 [SMILES: O=C(O)c1ccc2c(c1)B(O)OC2]

Formula II

In some embodiments, the compound of Formula I can be selected from the group consisting of:

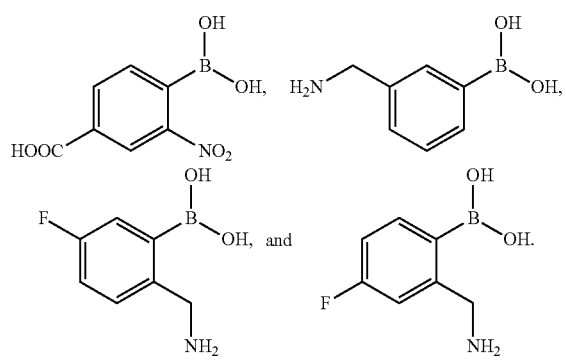

In some embodiments, the boronic acid compound, e.g., the compound of Formula I, can be conjugated to a dendrimer. A person of ordinary skill in the art would know that dendrimers are highly branched, star-shaped macromolecules that can have nanometer-scale dimensions. Dendrimers can be generally defined by three components: a central core, an interior dendritic structure (the branches), and an exterior surface with functional surface groups. The varied combination of these components can yield products of different shapes and sizes with shielded interior cores. Accordingly, in some embodiments, the dendrimer can be, for example, a polyamidoamine (PAMAM) dendrimer, poly (propylene imine) (PPI) dendrimer, and the like. In some embodiments, the boronic acid compound of Formula II can be conjugated to a dendrimer.

In some embodiments, one boronic acid compound molecule is bound to each dendrimer. In some embodiments, a plurality of boronic acid compound molecules is bound to each dendrimer. The number of boronic acid compound molecules bound to one dendrimer can be proportional to the dendrimer size. In some embodiments where a plurality of boronic acid compound molecules are bound to a single dendrimer, multiple glycocompounds can interact with the plurality of boronic acid compound molecules bound to the single dendrimer. Without wishing to be bound by theory, it is thought that multiple glycans from one glycocompound synergistically interact with different boronic acid compound molecules on a single dendrimer. The dendrimer size can increase with the number of rounds of synthesis, as well as the number of boronic acid compound molecules after conjugation. In some embodiments, the number of glycocompound interactions increases linearly with each round of dendrimer synthesis from a first cycle to a fourth cycle of synthesis (where when the cycle number is zero, the boronic acid compound is not conjugated to a dendrimer, i.e., the boronic acid compound is free of dendrimer). In some embodiments, after four synthesis cycles, there can be no significant increase in glycocompound interaction.

In some embodiments, the dendrimer can be bound to a bead, such as for example and not limitation, a magnetic bead. The magnetic bead can comprise, for example, silanized iron oxide that can be further derivatized. For example, the magnetic bead can be an amine derivatized bead, a carboxyl derivatized bead, and the like.

Some embodiments of the present disclosure can be a method for identifying a plurality of distinct glycosylation sites located on the glycocompound. In some embodiments, the method can comprise identifying a plurality of distinct O-glycosylation sites, N-glycosylation sites, and/or combinations thereof, wherein the sites can be glycosylation sites on a glycocompound, for example, a glycopeptide, a glycoprotein, and the like.

One advantage of some embodiments of the present disclosure is the ability to identify and analyze glycocompounds without sample restriction. That is, the disclosed methods can be applied for glycocompound analysis in any sample, including, but not limited to, whole cell lysates, animal tissues, plant and clinical samples (such as for example and not limitation, bodily fluid samples (e.g., blood, saliva, sputum, cerebrospinal fluid), and tissue samples). For instance, in some embodiments, glycocompounds can be enriched in in human cells and the identity and structure of glycans and glycosylation sites can be analyzed in human cells. Without wishing to be bound by theory, it is thought that due to the diversity of glycan structure, it can be more challenging to globally analyze glycoproteins in human cells. Accordingly, in some embodiments, the compositions and methods disclosed herein can be applied to human cells. In some embodiments, the glycocompounds can be enriched in human cells. In some embodiments, the glycocompounds and respective O- and/or N-glycosylation sites can be identified and analyzed in human cells. In some embodiments, glycan structure can be analyzed and determined in human cells.

Some embodiments of the present disclosure can include a method comprising enriching a glycocompound by contacting the glycocompound with a boronic acid compound to form a glycocompound-boronic acid-complex; and identifying a glycosylation site located on the glycocompound. In some embodiments, the method can comprise identifying a plurality of glycosylation sites located on the glycocompound, e.g., N- or O-glycosylation sites, or a combination thereof. In some embodiments, the boronic acid compound can be conjugated to a dendrimer. In some embodiments, the boronic acid compound can be a compound of Formula II. In some embodiments, the boronic acid compound of Formula II can be conjugated to a dendrimer.

Some embodiments of the present disclosure can include a method for identifying a plurality of glycosylation sites located on a glycocompound. In some embodiments, the method can include contacting the glycocompound with a boronic acid compound to form a glycocompound-boronic acid complex. In some embodiments, the contacting step can be performed at a basic pH, e.g., a pH of about 7 to about 14. In some embodiments, the method can further comprise washing the glycocompound-boronic acid-complex to enrich glycocompound. In some embodiments, the method can further comprise releasing the glycocompound from the boronic acid compound. In some embodiments, the releasing step can be at an acidic pH, e.g., at a pH of from about 0 to about 7. In some embodiments, the releasing step can be at a pH of from about 0 to about 7. In some embodiments, the releasing step can be at a pH of from about 0 to about 6. In some embodiments, the releasing step can be at a pH of about 6, about 5, about 4, about 3, about 2, about 1, or about 0. In some embodiments, the releasing step can be at a pH of about 5. In some embodiments, the method can further comprise cleaving at least one glycan component from the glycocompound to form a free glycan. In some embodiments, the cleaving step can comprise contacting the enriched glycocompound with a peptide-N-glycosidase F (PNGase F) to form a free N-glycan. In some embodiments, the method can further comprise analyzing a plurality of glycosylation sites located on the glycocompound. In some embodiments, the glycosylation sites can be N-glycosylation sites, O-glycosylation sites, or combination thereof. In some embodiments, the analyzing step can comprise analyzing the free glycans. In some embodiments, the glycosylation sites can be identified by mass spectrometry. In some embodiments, the free glycans can be analyzed by mass spectrometry. In some embodiments, the glycosylation sites can be identified by liquid chromatography-mass spectrometry, e.g., LC-MS and/or LC-MS/MS. In some embodiments, the free glycans can be analyzed by liquid chromatography-mass spectrometry, e.g., LC-MS and/or LC-MS/MS.

Some embodiments of the present disclosure include a composition comprising a dendrimer-boronic-acid (DBA) complex that can comprise a compound of Formula I conjugated to a dendrimer to form a DBA complex and a glycocompound reversibly bound to the DBA complex.

In some embodiments, the compound of Formula I can be:

Formula I wherein $R_1$ can be selected from unsubstituted or substituted alkyl, unsubstituted or substituted heteroalkyl, unsubstituted or substituted aryl, and unsubstituted or substituted heteroaryl; and $R_2$ can selected from H, a substituted or unsubstituted $C_1$-$C_6$ alkyl, and a $C_1$-$C_3$ alkylene, which together with $R_1$ can form a five- to seven-membered ring. In some embodiments, $R_1$ can be an unsubstituted or substituted aryl and $R_2$ can be H. In some embodiments, $R_1$ can be an unsubstituted or substituted aryl and $R_2$ can a methylene, which together with $R_1$ can form a five-membered ring.

In some embodiments, the compound of Formula I can be:

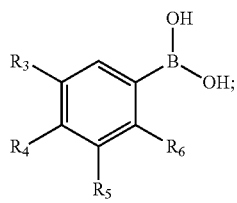

wherein $R_3$, $R_4$, $R_5$, and $R_6$ can be independently selected from H, halogen, —C(=O)—OH, —($C_{1-8}$-alkylenyl)-$NH_2$, and —$NO_2$; and at least one of $R_3$, $R_4$, $R_5$, and $R_6$ is not H. In some embodiments, $R_6$ can be selected from —$NO_2$, and —($C_{1-8}$-alkylenyl)-$NH_2$; and one of $R_3$ and $R_4$ can be independently selected from halogen, —C(=O)—OH, and H. In some embodiments, $R_6$ can be —($C_{1-8}$-alkylenyl)-$NH_2$; one of $R_3$ and $R_4$ can be halogen; and $R_5$ can be H. In some embodiments, $R_6$ can be —$CH_2$—$NH_2$; $R_3$ can be H; $R_4$ can be F and $R_5$ can be H. In some embodiments, $R_6$ can be —$CH_2$—$NH_2$; and one of $R_3$ can be F; $R_4$ can be H and $R_5$ can be H. In some embodiments, $R_3$ can be —$CH_2$—$NH_2$, and $R_4$, $R_5$, and $R_6$ can each be H. In some embodiments, the compound of Formula I can be:

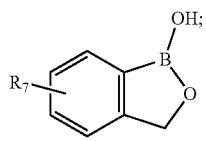

wherein $R_7$ is selected from C(=O)—OH, or —$CH_2$—$NH_2$. In some embodiments, the compound of Formula I can be Formula II

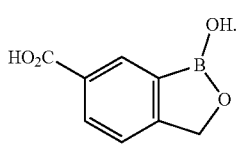

In some embodiments, the compound of Formula I can be selected from the group consisting of:

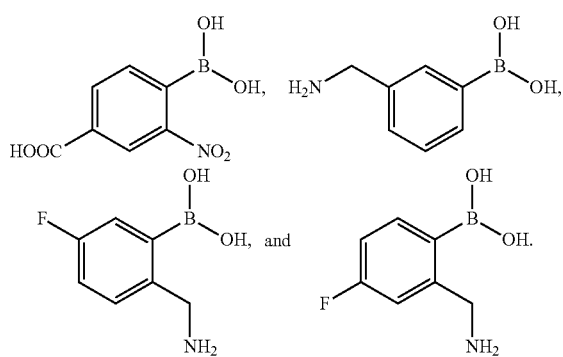

In some embodiments, the boronic-acid-dendrimer (DBA) complex can be reversibly bound to a glycan component of the glycocompound. In some embodiments, the DBA complex can be reversibly bound to at least one hydroxyl moiety on the glycan component of the glycocompound.

In some embodiments, the dendrimer-boronic-acid (DBA) complex can comprise a bead, such as for example and not limitation, a magnetic bead, to form a dendrimer-boronic-acid (DBA) bead. In some embodiments, the bead (e.g., magnetic bead) can be conjugated to the dendrimer component of the DBA complex. In some embodiments, the DBA complex or DBA bead comprises a plurality of boronic acid compounds conjugated to a single dendrimer.

Some embodiments of the present disclosure include methods for enriching O-GlcNAcylated proteins, and identifying glycosylation sites on the same. Protein O-GlcNAcylation was discovered more than three decades ago, and it has been reported to be involved in many cellular events, from regulating cell signaling to gene expression. It can be challenging to enrich O-GlcNAcylated proteins because only one sugar (GlcNAc) is bound to S or T, and this sugar does not contain a cis-1,2-diol. Although boronic acid can interact with sugars without cis-1,2-diols, such as glucose and GlcNAc, the interaction is weak, and enrichment is therefore less effective. The inventors of the present disclosure surprisingly found that the disclosed methods and compositions can be useful for effectively enriching O-GlcNAcylated proteins, and identifying glycosylation sites. In some embodiments, O-GlcNAcylated proteins can be enriched with the DBA beads disclosed herein. Without wishing to be bound by theory, it is thought that the effective enrichment of O-GlcNAcylated peptides may be attributed to the synergistic interactions with DBA beads. Multiple sugars from one glycan can synergistically interact with different benzoboroxole molecules on a single dendrimer bead. Although there is no cis-1,2-diol in GlcNAc, multiple hydroxyl groups in each GlcNAc may form reversible covalent bonds with several boronic acid compound, e.g., benzoboroxole (Formula II), molecules on a dendrimer bead, as shown in FIG. 6c. The synergistic interactions can dramatically facilitate the enrichment of O-GlcNAcylated peptides with DBA

EXAMPLES

The following materials and procedures were used for each of the Examples described herein.

Materials.

Complete protease inhibitors were purchased from Roche Applied Sciences and sequencing grade trypsin was from Promega. Dulbecco's Modified Eagle's Medium (DMEM), phosphate buffered saline (PBS), N-(3-dimethylaminopropyl)-N'-ethylcarbodiimide hydrochloride (EDC), 4-carboxy-2-nitrophenylboronic acid, (2-aminomethyl-5-fluoro) phenylboronic acid hydrochloride, 2-aminomethyl-4-fluorophenylboronic acid hydrochloride, trifluoroacetic acid, formic acid (FA), trimethylamine (TEA), piperidine (pyp), methanol, chloroform, dichloromethane (DCM), acetonitrile (ACN), and dimethylsulfoxide (DMSO) were from Sigma-Aldrich. 3-aminomethylphenylboronic acid hydrochloride was from Frontier Scientific Inc. 5-carboxybenzoboroxole (e.g., "Formula II comprising a carboxyl group to bind to a magnetic bead) and 1-hydroxy-7-azabenzotriazole (HOAt) were purchased from AK Scientific, Inc. (2,5-dioxopyrrolidin-1-yl) (2S)-2-(9H-fluoren-9-yl-methoxycarbonylamino)-6-[(2-methylpropan-2-yl)oxycarbonylamino] hexanoate (Fmoc-L-Lys(Boc)-OSu) and (S)-2,5-dioxopyrrolidin-1-yl 2,6-bis((tert-butoxycarbonyl) amino) hexanoate (Boc-Lys(Boc)-OSu) were from Ark Pharm, Inc.

and Sigma-Aldrich. MagnaBind™ amine derivatized beads, MagnaBind™ carboxyl derivatized beads, and fetal bovine serum (FBS) were bought from Thermo Fisher Scientific.

Magnetic Beads Derivatization.

MagnaBind™ carboxyl (or amine) derivatized beads were washed with DMSO three times. EDC was added to the beads slurry and incubated end-over-end for 10 min; HOAt was subsequently added, and the reaction mixture was further incubated for one hour. HOAt-activated beads were washed with DMSO twice and incubated overnight with different amino boronic acids in DMSO containing 3.0% triethylamine (TEA). The boronic acid functionalized beads were washed with DMSO twice and 20% ACN three times and stored in 20% ACN for further use.

For dendrimer boronic acid derivatization, the solvent containing the MagnaBind™ amine derivatized beads was gradually changed from water to isopropanol to finally DCM (Supplementary FIGS. 1 and 2). Then Fmoc-L-Lys(Boc)-OSu was reacted with the amine beads in DCM containing 0.3% TEA overnight. On the following day the beads were washed with DCM three times, and the Boc protection group was removed by incubation of beads in 50% TFA in DCM at room temperature for two hours. The beads were washed with DCM three times and one time with 3% TEA in DCM. To continue the derivatization, Boc-Lys(Boc)-OSu was added to the bead DCM solution followed by the addition of TEA (final concentration 3.0%). The reaction was carried out at room temperature with end-over-end rotation overnight. Then the Boc group was deprotected by 50% TFA as mentioned above. The Boc-Lys(Boc)-OSu conjugation step was repeated twice. Then the Fmoc groups were removed by mixing the functionalized beads in 50% piperidine DCM solution at room temperature for 30 minutes. Finally, all free amine groups were coupled with 5-carboxybenzoboroxole through EDC HOAt chemistry as described above. The resulting dendrimer-boronic-acid (DBA) beads comprised boronic acid compounds of Formula II conjugated to the dendrimer.

Yeast Cell Culture and Protein Extraction.

Yeast cells (strain BY4742, MAT alpha, derived from S288c) were grown in yeast extract peptone dextrose (YPD) media until they reached log-phase (optical density (OD) was about 1.0 at 600 nm). For biological duplicate experiments, cells were grown independently. Yeast cells were harvested by centrifugation and resuspended in a buffer containing 50 mM 4-(2-hydroxyethyl)-1-piperazineethane-sulfonic acid (HEPES), pH 7.4, 150 mM NaCl, 0.5% sodium deoxycholate (SDC) and protease inhibitor cocktail (one tablet (complete mini, Roche) per 10 ml lysis buffer) at 4° C. Cells were lysed using the MiniBeadbeater (Biospec) at maximum speed, three cycles of 30 s each, with 2 min pauses between cycles to avoid overheating the lysates. After centrifugation, lysates were transferred to new tubes, and the protein concentration in the lysate was determined by BCA protein assay (Pierce).

Human Cell Culture and Protein Extraction.

MCF7, HEK 293T and Jurkat cells (American Type Culture Collection (ATCC)) were cultured following the instructions provided by ATCC. Once MCF7 and HEK 293T cells reached 80% confluency, cells were washed with PBS twice and harvested by scraping. Jurkat cells were harvested by centrifugation and then washed with PBS. Cell pellets were suspended in the ice-cold RIPA buffer (50 mM HEPES, pH=7.4, 150 mM NaCl, 0.5% SDC, benzonase (25 U/mL), and protease inhibitor cocktail) and incubated end-over-end for 1 hour at 4° C. After complete solubilization of nuclei and digestion of genomic DNA, the lysate was centrifuged at 25,000 g for 10 minutes. The supernatant was collected and the protein concentration was measured by BCA protein assay.

Protein Extraction from Mouse Brain Tissues.

For mouse brain samples, brain tissues from two $C_{57}BL/6$ mice (3 and 6 months) were frozen in liquid nitrogen and homogenized in the RIPA buffer mentioned above. The mixtures were incubated on ice for an hour, and then clarified by centrifugation at 5,000 g for 20 minutes. Half of the supernatants (~8 mg proteins per experiment) were used for protein glycosylation analysis.

Protein Alkylation and Digestion.

Lysates from yeast, human cells, or mouse brain tissue were reduced with 5 mM dithiothreitol (DTT) (56° C., 25 minutes) and alkylated with 15 mM iodoacetamide (RT, 30 minutes in the dark). Proteins were purified by the methanol-chloroform precipitation method. The purified proteins were digested with Lys-C (Wako) at a protein:enzyme ratio of ~100:1 in 50 mM HEPES, pH=8.2, 1.6 M urea, 5% ACN at 31° C. overnight, and then 10 ng/μL trypsin (Promega) for 4 h. Digestion was quenched by the addition of TFA to a final concentration of 0.1%, and precipitate was removed by centrifugation at 5,000 g for 10 min. The supernatant was collected, and peptides were purified using a Sep-Pak tC18 cartridge (Waters).

Glycopeptide Enrichment.

For boronic acid derivative experiments, mammalian peptides were dissolved in 100 mM ammonium acetate buffer and incubated for one hour with different boronic acid derivatized magnetic beads at room temperature. After incubation, the beads were washed with the binding buffer, and enriched peptides were eluted first by incubation with a solution containing $ACN:H_2O:TFA$ (50:49:1) at 37° C. for 30 min. Then the peptides were eluted two more times through incubation with 5% formic acid at 56° C. for 5 min each time. For the enrichment of peptides from yeast, human cells or mouse brain tissues using DBA, ~10 mg of peptides were used in each experiment and incubated with DBA beads in DMSO containing 0.5% TEA, then washed five times using a buffer containing 50% DMSO and 50% 100 mM ammonium acetate (pH=11). Glycopeptides were then eluted as described above.

For lectin enrichment, ConA and WGA-conjugated agarose beads (Vector Laboratories) were washed five times using the enrichment buffer (20 mM tris-base pH=7.4, 0.15 M NaCl, 1 mM $MgCl_2$, 1 mM $CaCl_2$), and 1 mM $MnCl_2$). Peptides were dissolved in the enrichment buffer, mixed with the lectin beads, and vortexed under 37° C. for an hour. The beads were then washed again with the enrichment buffer for five times before glycopeptide elution using the elution buffer (0.2 M α-methyl mannoside, 0.2 M α-methyl glucoside, 0.2 M galactose, and 0.5 M N-Acetyl-D-Glucosamine in PBS). The elution was performed twice with vortex for half an hour each, and the eluents were combined.

For HILIC enrichment, SeQuant® ZIC-HILIC SPE cartridges (the Nest Group) were washed with ten column volumes of 1.0% TFA in water, followed by three washes with the loading buffer (1.0% TFA in 80% ACN, 20% $H_2O$). Peptides were loaded onto the column in the loading buffer using a slow flow rate. The flow-through was re-loaded onto the column once. The column was then washed with the loading buffer three times. Glycopeptides were eluted using 1.0% TFA in water three times, and the eluents were combined.

Glycopeptide PNGase F Treatment and Fractionation.

The enriched samples were dried in a lyophilizer overnight. The completely dried samples were dissolved in 40 mM ammonium bicarbonate in heavy-oxygen water ($H_2^{18}O$) and treated with PNGase F (lyophilized powder from Sigma Aldrich) at 37° C. for 3 hours. For optimization experiments, after deglycosylation, peptide samples were purified using a stage tip. For all other experiments, enriched glycopeptides were desalted using a tC18 Sep-Pak cartridge, and then subjected to fractionation using high-pH reversed phase HPLC (pH=10). The sample was separated into 10 fractions using a 4.6×250 mm 5 μm particle reversed phase column (Waters) with a 40-min gradient of 5-50% ACN with 10 mM ammonium acetate. Every fraction was further purified with stage tip before LC-MS/MS.

LC-MS/MS Analysis.

Fractionated and purified peptide samples were resuspended in a solvent of 5.0% ACN and 4.0% FA, and 4 μL was loaded onto a microcapillary column packed with C18 beads (Magic C18AQ, 3 μm, 200 Å, 75 μm×16 cm) using a WPS-3000TPLRS autosampler (UltiMate 3000 thermostatted Rapid Separation Pulled Loop Wellplate Sampler, Dionex). Peptides were separated by reversed-phase chromatography using an UltiMate 3000 binary pump with a 90-min gradient of 4-30% ACN (in 0.125% FA) and detected in a hybrid dual-cell quadrupole linear ion trap-orbitrap mass spectrometer (LTQ Orbitrap Elite, Thermo-Fisher) using a data-dependent Top20 method. For each cycle, one full MS scan (resolution: 60,000) in the Orbitrap at $10^6$ AGC target was followed by up to 20 MS/MS in the LTQ for the most intense ions. The isolation window was 2 Da, which is the most commonly used, and the activation energy was 40% normalized collision energy (NCE), which was obtained through testing different NCEs to acquire the best results for the machine used here. Selected ions were excluded from further analysis for 90 s. Ions with a single or unassigned charge were not sequenced. Maximum ion accumulation times (Maximum IT) were 1000 ms for each full MS scan and 50 ms for MS/MS scans. For protein O-glycosylation analyses, the data was collected using a Q-Exactive Plus Orbitrap mass spectrometer with a two-hour LC gradient. Higher-energy collisional dissociation (HCD) was used as the fragmentation method with the following parameters: $10^6$ AGC target for full MS and $2*10^5$ AGC target for $MS^2$, 100 ms maximum IT, 2.0 Da isolation window, and 30% NCE. The dynamic exclusion time was set to 60 sec. Both full MS and $MS^2$ were collected in the Orbitrap cell with high mass accuracy and high resolution, which contribute to confident identification of O-glycopeptides.

Database Searches and Data Filtering.

The raw files were converted into mzXML format prior to the database search. The SEQUEST algorithm (version 28) was used to search all MS/MS spectra against either a database containing sequences of yeast (*Saccharomyces cerevisiae*) proteins downloaded from SGD (http://www.yeastgenome.org/) or human (*Homo sapiens*) proteins downloaded from UniProt. The following parameters were used for the database search: 10 ppm precursor mass tolerance; 1.0 Da product ion mass tolerance; fully tryptic digestion; up to two missed cleavages; variable modifications: oxidation of methionine (+15.9949) and $^{18}O$ tag of Asn (+2.9883); fixed modifications: carbamidomethylation of cysteine (+57.0214). In order to estimate the FDR of peptide identification, both forward and reversed orientations of each protein sequence were listed in the database, and the target-decoy method was employed[58]. To distinguish between correct and incorrect peptide identifications, linear discriminant analysis (LDA) was utilized with several parameters such as XCorr, ΔCn, and precursor mass error[68]. After scoring, peptides shorter than seven amino acid residues were discarded, and the remaining peptide spectral matches were controlled to have less than 1.0% FDR. When determining FDRs of the final data set, only glycopeptides were considered.

For O-glycopeptide identification, we used Byonic™ software. Some parameters are similar as above. For yeast intact O-glycopeptide analysis, up to ten mannoses per glycan were searched for raw files. In order to control false positive rates, every peptide was required to have ≤0.001 for 1 D PEP (one dimensional posterior error probability) and >4 for |Log Prob| (the absolute value of the log 10 of the posterior error probability)[69]. The Score of identified glycopeptide must be higher than 300, and the mass accuracy is less than 10 ppm. The PEP takes into account 10 features, including the Byonic™ score, delta score, precursor mass error, digestion specificity, etc. Requiring |Log Prob| to be larger than 4 means the P value is $<10^{-4}$, based on Neyman-Pearson hypothesis testing. These are very stringent criteria for filtering. For example, for protein O-GlcNAcylation analysis, after filtering, there was no reverse hit in the final datasets. For glycoproteins identified in each type of cells, we performed subcellular compartment analysis based on the protein location information downloaded from Uniprot (uniprot.org).

Protein glycosylation site localization. In order to evaluate the confidence of the glycosylation site assignment, a Modscore was calculated for each identified glycopeptides, which is similar to Ascore. An algorithm considering all possible glycosylation sites of a peptide was used to generate the Modscore. It examines the presence or absence of MS/MS fragment ions unique to each glycosylation site and indicates the likelihood that the best site match is correct when compared with the next best match. Sites with Modscore ≥19 (P≤0.01, cumulative binomial probability) were considered to be confidently localized.

Example 1—Enhancing Glycopeptide Enrichment with BA Derivatives

Figure 1B:
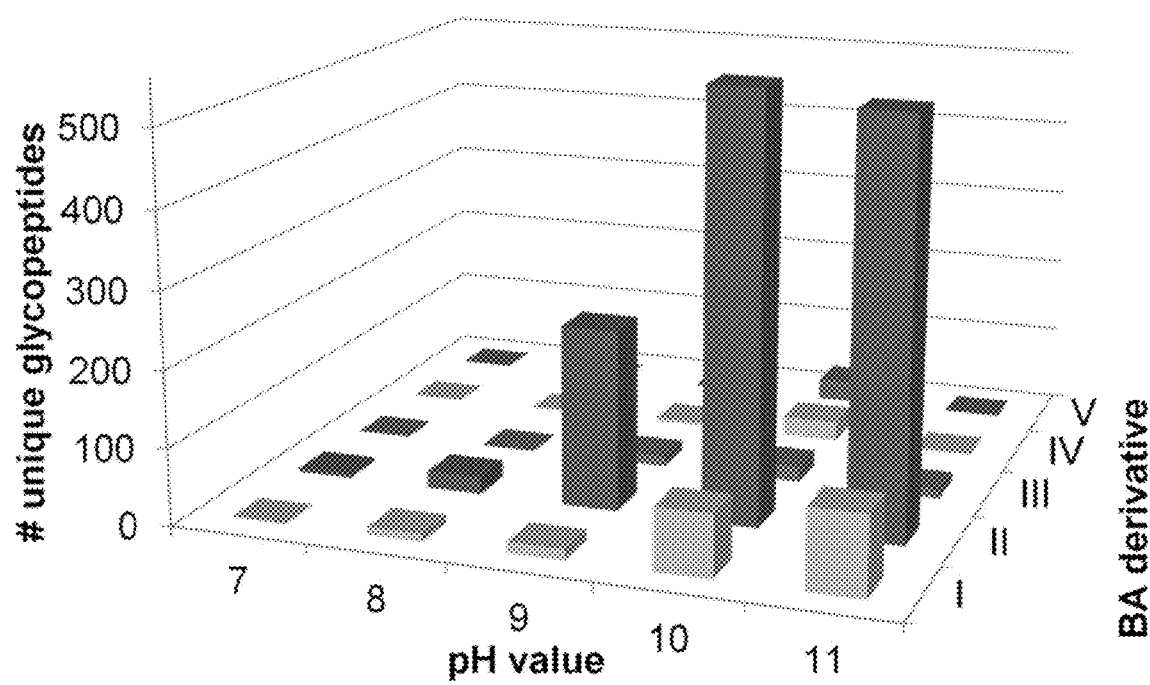

The structures of boronic acid (BA) derivatives tested here are displayed in FIG. 1a. In parallel experiments starting with the same amount of purified peptides from human cells (HEK 293T), enrichment with derivatives I, IV and V resulted in slightly more unique N-glycopeptides compared to phenylboronic acid (III) (FIG. 1b).

The BA derivatives were also examined at different pH values and compared the number of unique identified N-glycopeptides. Very few glycopeptides were identified at pH=7 or 8 with any BA derivative. For all derivatives, the optimal pH was 10 or 11, as shown in FIG. 1b. The derivatives IV and V enriched slightly more unique glycopeptides compared to phenylboronic acid (III). Although the $pK_a$ of derivative I (9.2) is similar to that of phenylboronic acid (9.0), enrichment with I resulted in the identification of more unique glycopeptides. One possible reason is that the adjacent nitrogen may form an extra hydrogen bond with a nearby hydroxyl group on the glycan, which enhances the interactions between the BA derivative and glycans and facilitates the enrichment.

Among the five boronic acids tested, Formula II (benzoboroxole) allowed the identification of the greatest number of glycopeptides. The method based on Formula II (benzoboroxole) was systematically optimized for site-specific and global analysis of glycoproteins in combination with MS, and the results were dramatically improved compared to any other boronic acids tested.

Example 2A—Synergistic Interactions to Increase Glycopeptide Coverage

A dendrimer was synthesized as the platform for synergistic interactions such that the number of benzoboroxole (Formula II) molecules bound to a dendrimer could be easily adjusted. More importantly, the dendrimer branches also provide structural flexibility to enhance the synergistic interactions.

Figure 2A:
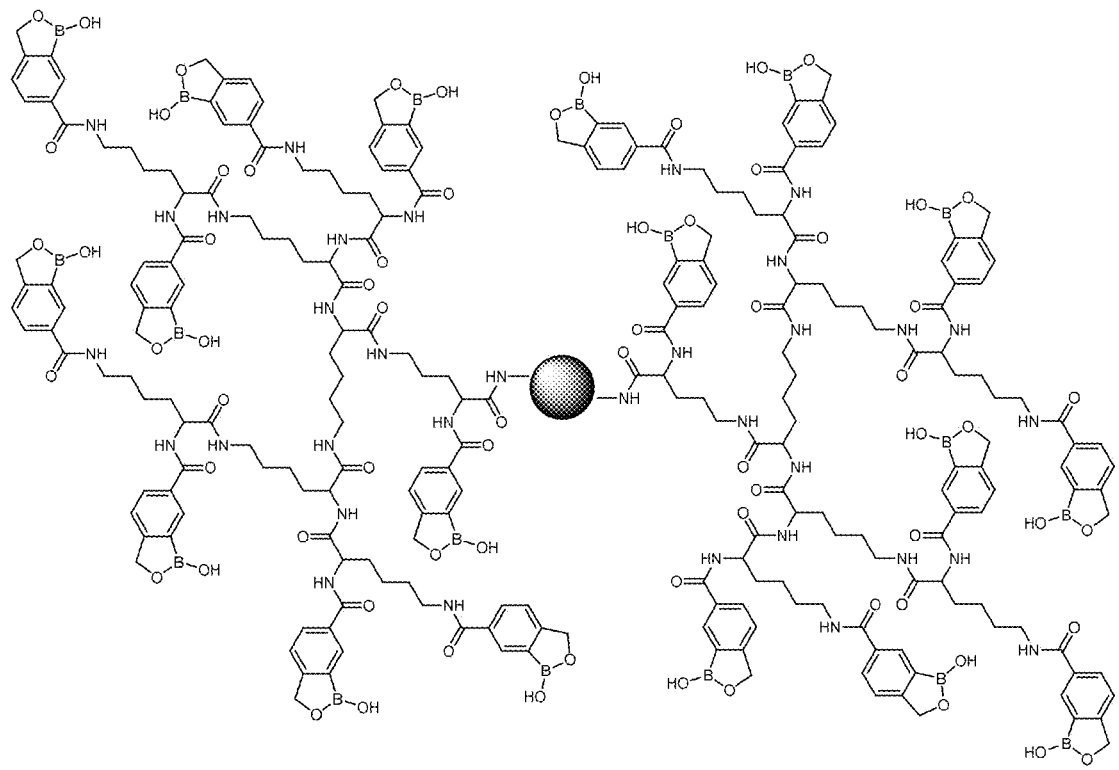
FIG. 2a-2d. Principle and experimental results of the synergistic interactions between the DBA beads and several sugars from one glycopeptide.
Figure 2B:
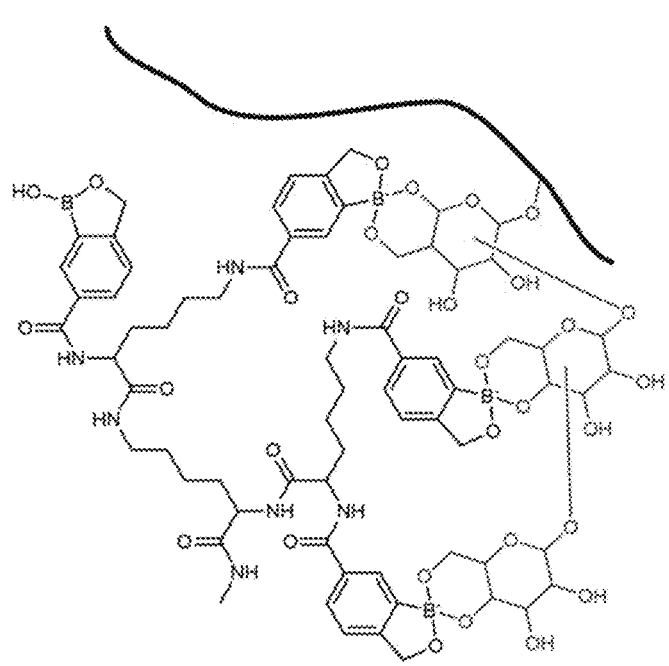
Figure 7:
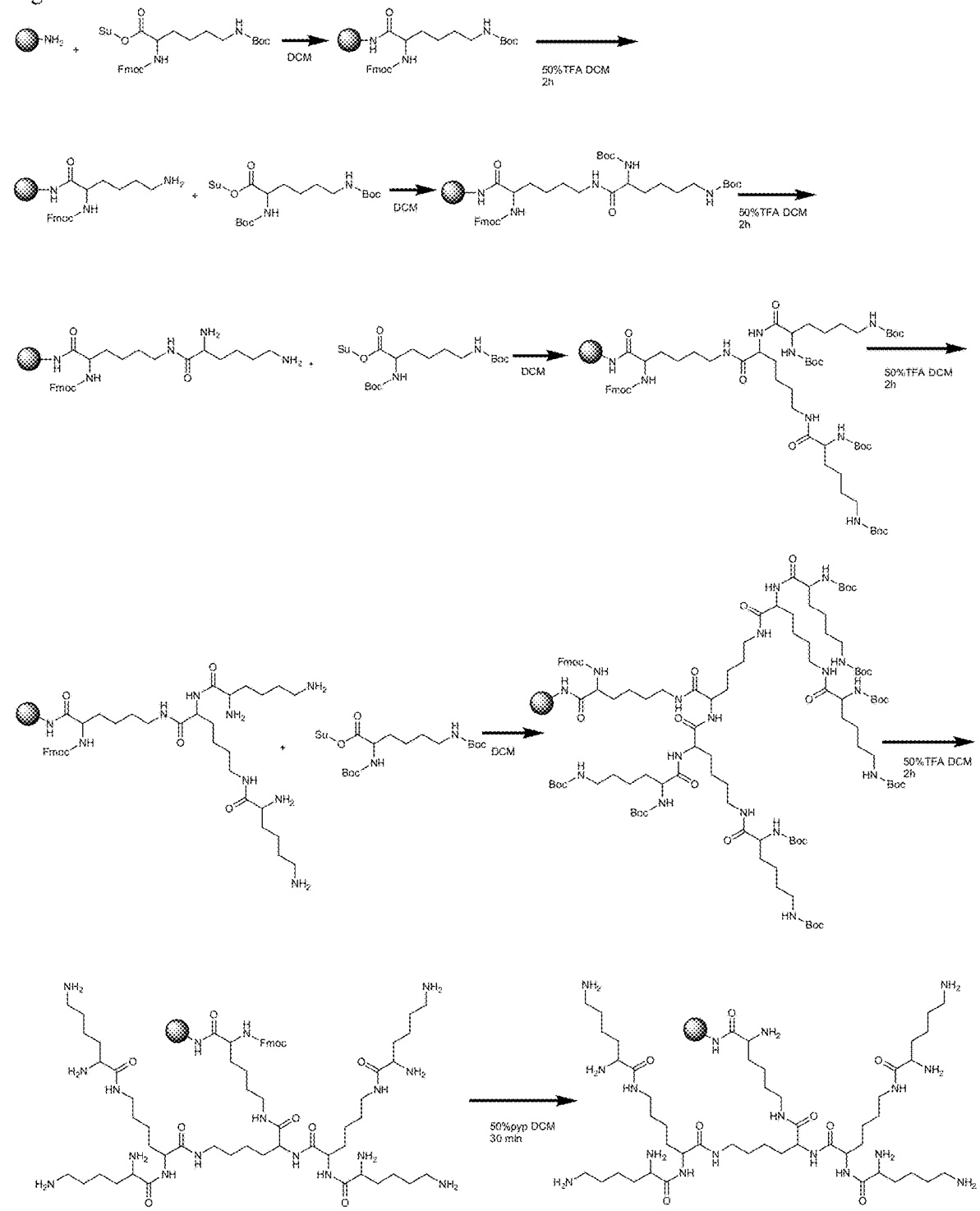
FIG. 7. Synthesis of the dendrimer with functional amine groups. Lysine molecules are used as the building blocks to construct the dendrimer on the amine-derivatized magnetic bead.
Figure 8:
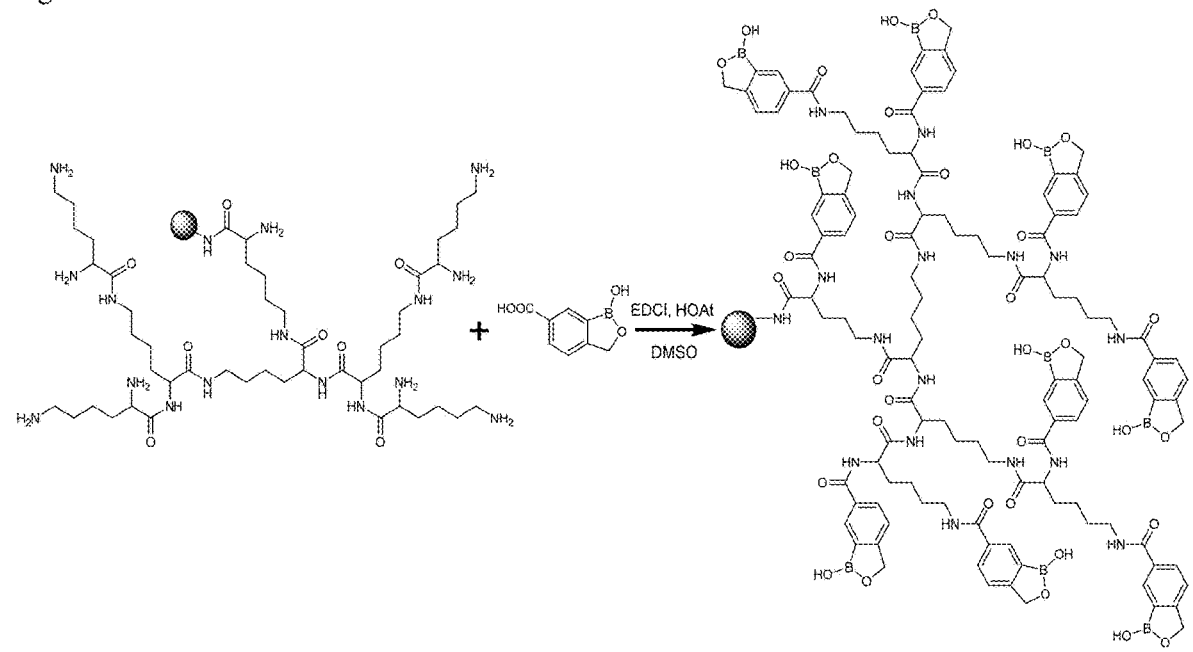
FIG. 8. Conjugation of benzoboroxole to the dendrimer. After synthesizing the dendrimer on the magnetic beads, benzoboroxole molecules are conjugated to the dendrimer.

The dendrimer was first synthesized and bound to magnetic beads, and next the BA derivative, benzoboroxole, was conjugated to the dendrimer (FIG. 7 and FIG. 8). Many benzoboroxole (Formula II) molecules were bound to one dendrimer, as shown in FIG. 2a, and the number of benzoboroxole (Formula II) molecules on one dendrimer bead was proportional to the dendrimer size. In this case, several sugars from one glycan can interact with multiple benzoboroxole (Formula II) molecules simultaneously (FIG. 2b).

Figure 2C:
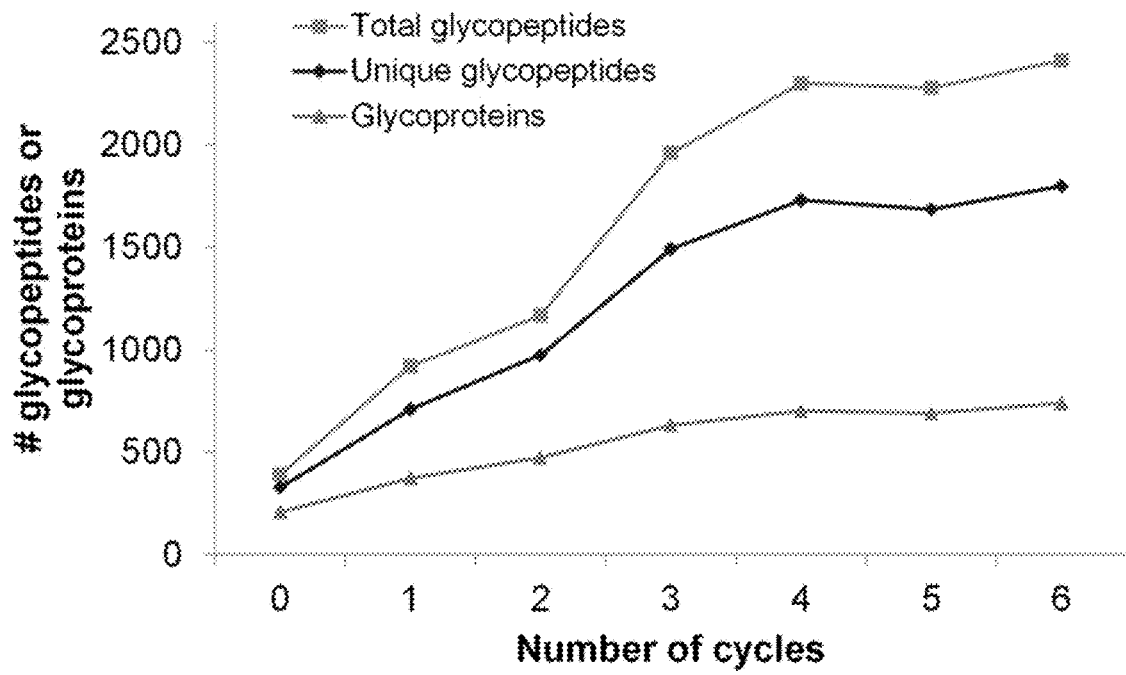
Figure 9:
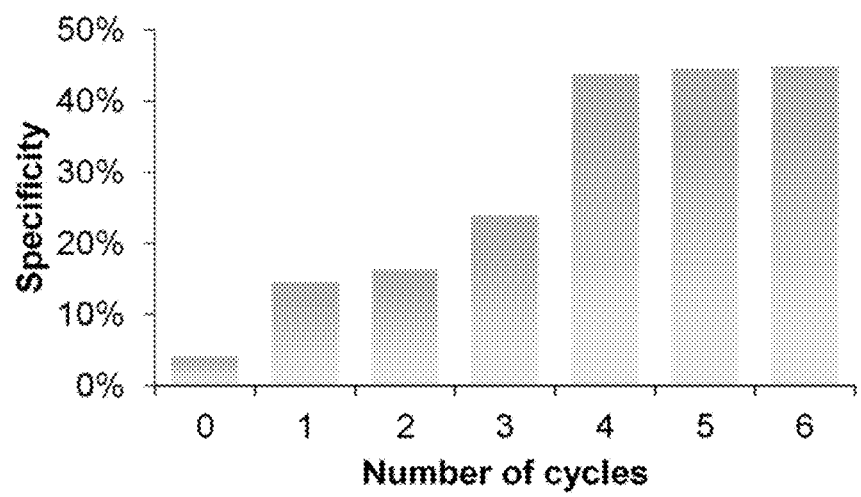
FIG. 9. The specificity of glycopeptide enrichment in correlation to the DBA bead size. The specificity of the N-glycopeptide identifications increases with the number of the dendrimer synthesis cycles, and it levels off after the fourth cycle. The overall specificity of glycopeptide enrichment should be higher considering that O-glycopeptides were also enriched.

Dendrimer size can have a large impact on the synergistic interactions, and the effect of dendrimer size was systematically evaluated. For the parallel experiments, the number of benzoboroxole (Formula II) molecules on the beads attempted to remain the same, and the amount of starting materials (peptides from HEK 293T cells) was also the same. In FIG. 2c, when the cycle number is zero, the magnetic beads are directly conjugated with benzoboroxole (Formula II) without a dendrimer. The dendrimer size increased with the number of rounds of synthesis, as well as the number of benzoboroxole (Formula II) molecules after conjugation. With dendrimer beads synthesized through one to four rounds of the reaction, the number of total N-glycopeptides, unique N-glycopeptides, and N-glycoproteins increased linearly (FIG. 2c). After four rounds of synthesis, the numbers were very comparable, and the specificity results have a similar trend (FIG. 9). Once the number of benzoboroxole (Formula II) molecules on a single bead reaches the threshold, larger dendrimers with more benzoboroxole (Formula II) molecules do not affect the synergistic interactions, which occurs after four rounds of synthesis.

Figure 2D:
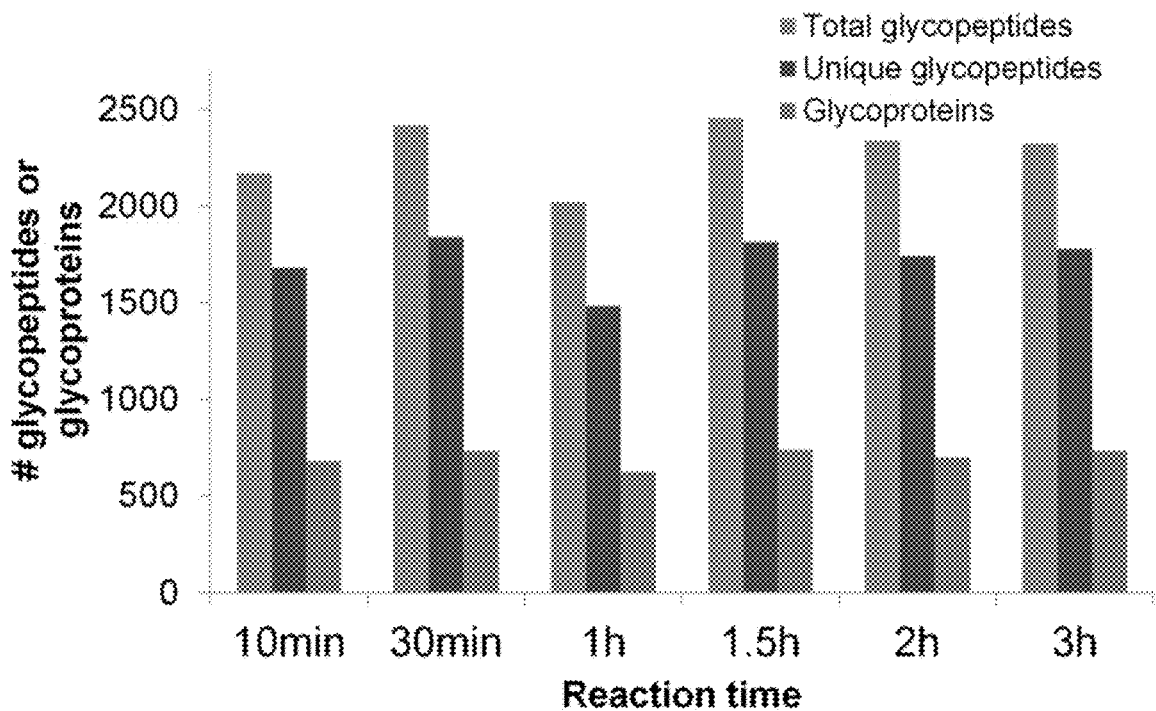

Since the enrichment reaction is quick and the conditions are mild, prolonging the reaction time does not have negative effects on glycopeptide identification. As shown in FIG. 2d, similar number of unique N-glycopeptides and glycoproteins were identified when the incubation time varied from 10 minutes to 3 hours.

Example 2B—Effect of Different Solvents on Glycopeptide Enrichment

Figure 10:
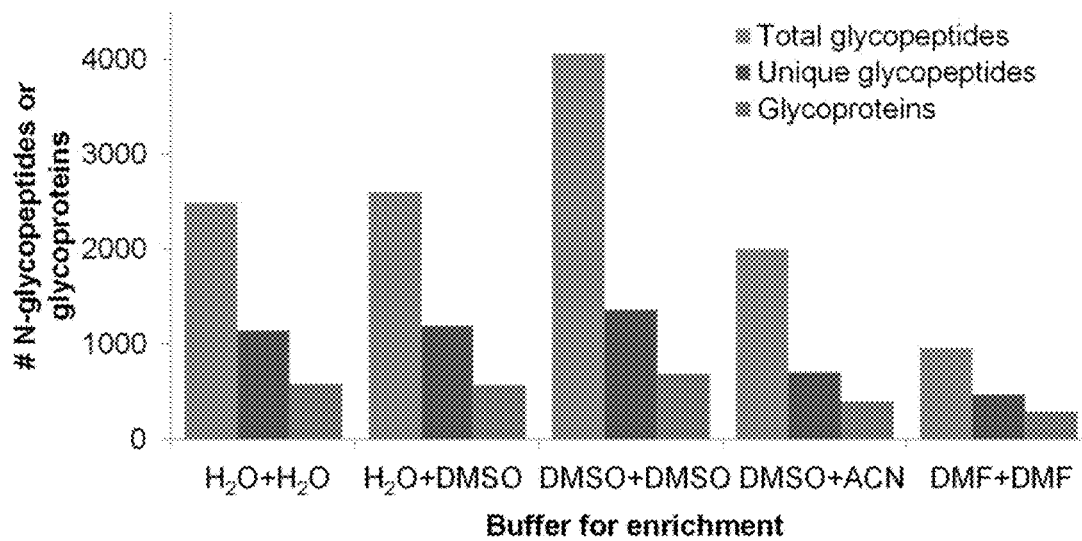
FIG. 10. Effect of solvents on glycopeptide enrichment from a human cell lysate (HEK 293T). Left bars—total glycopeptides, middle bars—unique glycopeptides and right bars—glycoproteins.

A variety of solvent combinations were tested for glycopeptide enrichment with DBA beads (FIG. 10). The pH of all aqueous solutions was adjusted to 11 using an ammonium acetate buffer. For each combination, the binding step of enrichment was performed for an hour in the first solution, and then the beads were washed five times in the second solution. The combination of "DMSO+DMSO" provided the highest enrichment efficiency with the identification of the most N-glycopeptides and glycoproteins. This is consistent with Le Chatelier's principle because water is the product of the reaction between the boronic acid derivative and sugars. Without water, the reaction shifts toward the direction of bond formation and becomes more complete.

Example 2C—Washing Buffer for Glycopeptide Enrichment Optimization

Figure 11:
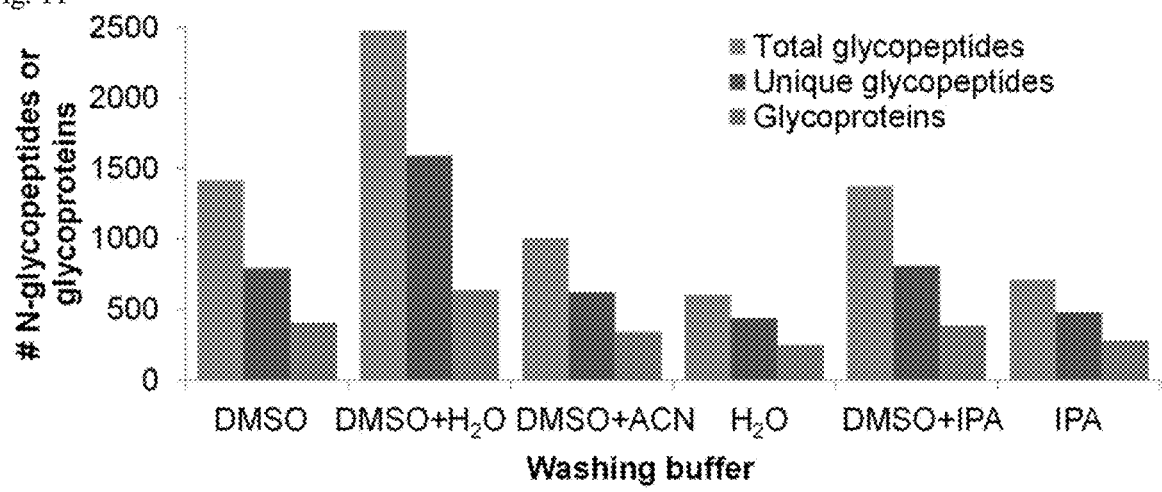
FIG. 11. Washing buffer optimization for glycopeptide enrichment. Left bars—total glycopeptides, middle bars—unique glycopeptides and right bars—glycoproteins.

Based on the results from Example 2B (FIG. 10), several washing buffers were tested, and the results are in FIG. 11. The enrichment was performed in DMSO containing 0.5% trimethylamine (TEA) for one hour, and then washed the beads with different buffer combinations. The enriched peptides were subsequently deglycosylated and analyzed by LC-MS/MS. The washing buffer containing 50% DMSO and 50% $H_2O$ (pH=11) outperformed all other combinations. The addition of water helped remove non-specifically bound peptides and increased the number of identified glycopeptides and glycoproteins.

Example 2D—Number of Washes for Glycopeptide Enrichment Optimization

Figure 12:
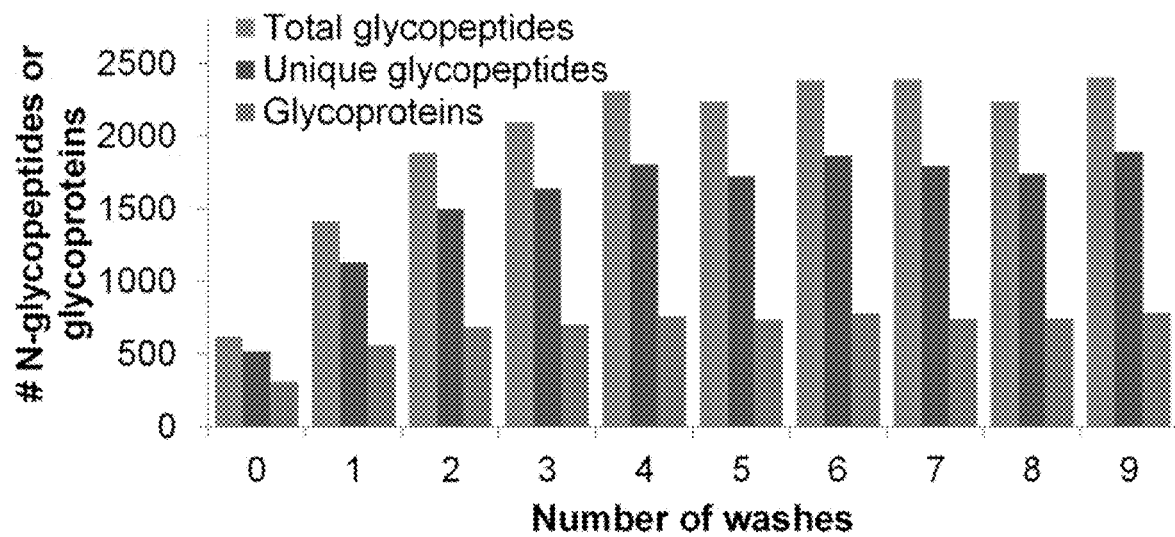
FIG. 12. The effect of washing times on glycopeptide enrichment. Left bars—total glycopeptides, middle bars—unique glycopeptides and right bars—glycoproteins.

Based on the previous results, the number of washes was optimized (0-9 washes). All parallel experiments started with about 0.25 mg mammalian peptides, which were enriched with the DBA beads in DMSO containing 0.5% TEA for one hour, and then the number of times the beads were washed with 50% DMSO and 50% $H_2O$ (pH=11) was varied. From 0 to 4 washes, a linear trend was found for N-glycopeptide and glycoprotein identifications because increasing the number of washes removed non-specifically bound peptides. After washing four times, there was no obvious change (FIG. 12). These results indicate that the interactions between DBA and glycans are very strong because washing more times did not result in the loss of glycopeptides.

Figure 13:
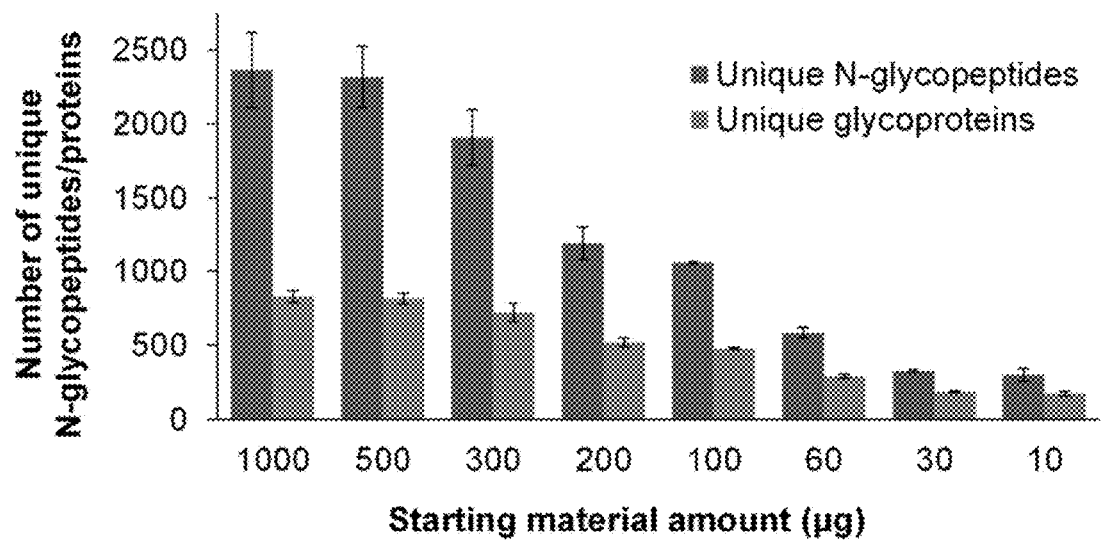
FIG. 13. Evaluation of the effect of sample size on the identification of glycopeptides and glycoproteins with the DBA enrichment followed by LC-MS analysis. Left bars—unique glycopeptides, and right bars—glycoproteins. The error bar represents the standard error of the mean calculated from duplicate experiments.

Example 2E—Effect of the Sample Size on the Identification of Glycopeptides and Glycoproteins Different amount of cultured MCF 7 cells were used to evaluate the sample size effect on the N-glycopeptide identification with the DBA enrichment. Duplicate experiments were performed. Cells in each group were harvested and the final protein amounts in the eight groups were around 10, 30, 60, 100, 200, 300, 500, and 1000 µg, respectively. After protein precipitation and digestion, the peptides were subject to DBA enrichment. The enriched glycopeptides were then purified and analyzed by LC-MS/MS. The data is presented in FIG. 13.

The lowest number of glycoproteins we identified in one MS run was about 200 from the 10 µg group among the samples tested here. When the sample amount is very small, the sample loss coming from every step may be a problem. For instance, when a very small volume of solvent (lysis buffer or digestion buffer) was used for cell lysis and protein digestion, the sample transfer from tube to tube could result in a considerable (relatively higher percentage) sample loss. More samples allowed us to identify higher numbers of unique glycopeptides and glycoproteins. After the protein amount reached ~300 µg, the increasing trend of the number of identified glycopeptides and glycoproteins slowed down, and both the 500 µg and 1000 µg groups yielded almost the same results. Besides the sample loss, the MS speed and sensitivity may also dramatically affect the number of unique glycopeptides identified. A machine with higher speed and sensitivity allows us to identify more glycoproteins using the same amount of material or the same number of glycoproteins using a lower amount of material. Of note, normally the protein digestion efficiency and peptide purification efficiency are lower than 100%, and therefore, the resulting peptide amounts subjected to the DBA enrichment in the current experiment should be slightly lower than the sample amounts shown in the figure.

Example 2F—Evaluation of the PNGase F Treatment Efficiency

Figure 19:
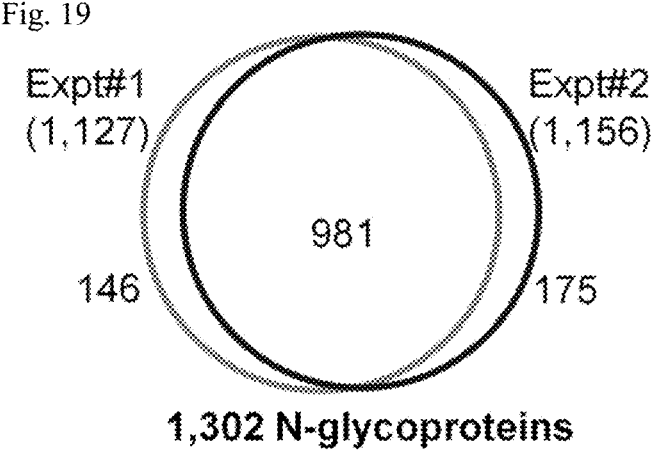
FIG. 19. Comparison of N-glycoproteins identified in MCF7 cells from duplicate experiments. A number of N-glycoproteins were identified in MCF7 cells using methods described herein.

The residual N-glycans after peptide-N-glycosidase F (PNGase F) treatment were also assessed, and duplicate experiments were performed to examine the percentage of residual N-glycans. The results demonstrated that the N-glycan removal efficiency with PNGase F within three hours was very high (FIG. 19).

Figure 14:
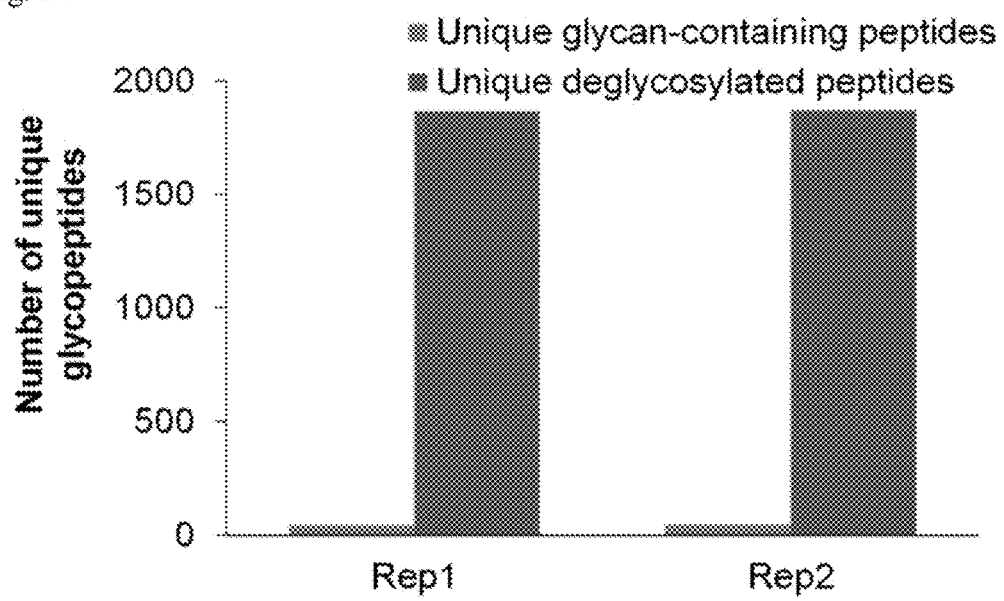
FIG. 14. Duplicate experimental results for assessing residual N-glycans after PNGase F treatment. Only about 2% N-glycopeptides contained residual glycans after the three-hour treatment (left bars—unique glycan-containing peptides, and right bars—unique deglycosylated peptides).

Regarding assessing the extent of residual N-glycans after PNGase F treatment, duplicate experiments were performed to examine the percentage of residual N-glycans (FIG. 14). The results indicated that the removal of N-glycans with PNGase F was effective. Peptides from MCF7 whole cell protein digestion were subject to enrichment with the DBA beads. The enriched glycopeptides were then treated with PNGase F in $H_2^{18}O$ for three hours. The purified peptides were analyzed using an online LC-MS/MS system with a Q-Exactive Plus mass spectrometer, and both full MS and MS/MS were recorded in the Orbitrap cell. Higher-energy collisional dissociation (HCD) was used as the fragmentation method. We searched for the deglycosylated peptides (2.9883 Da mass shift on N) and the N-glycan-containing peptides using Byonic. As a result, 44 unique glycan-containing peptides and 1,866 deglycosylated peptides were identified in the first experiment; 45 unique glycan-containing peptides and 1,871 unique deglycosylated peptides were identified in the second experiment. Overall, N-glycopeptides with residual N-glycans are only around ~2%, demonstrating that the three-hour PNGase F treatment was effective to remove N-glycans.

Control experiments were performed and the effect of spontaneous deamidation was found to be negligible under the treatment conditions (pH=7.5 and 37° C.) for three hours. For all experiments for protein N-glycosylation analysis, the treatment time was strictly controlled within three hours. Although a longer treatment time may lead to more complete removal of N-glycans and result in the identification of more N-glycosylation sites, spontaneous deamidation will cause higher false positive rates for protein N-glycosylation site identification.

Example 3—Comparison with Existing Lectin- and HILIC-Based Methods

Figure 3A:
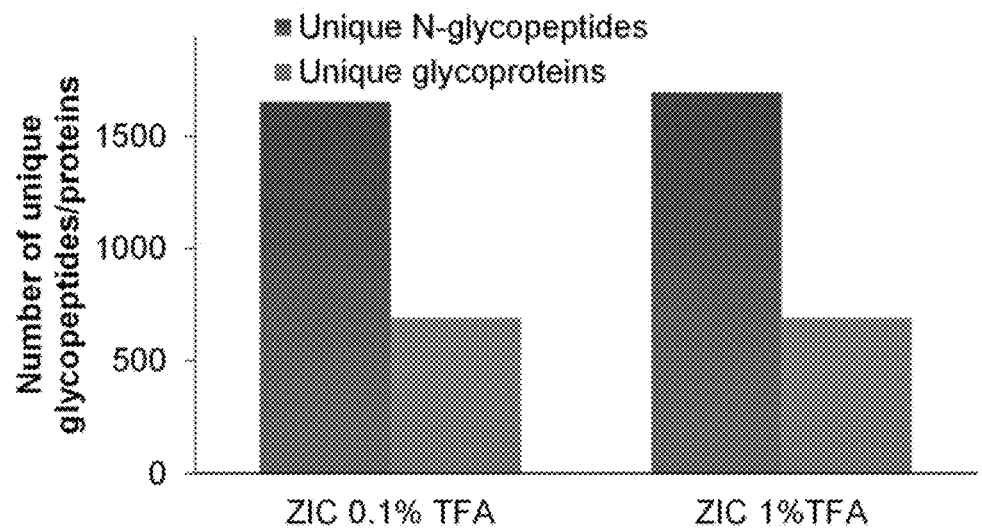
FIG. 3a-3c. Comparison of three enrichment methods.
Figure 3B:
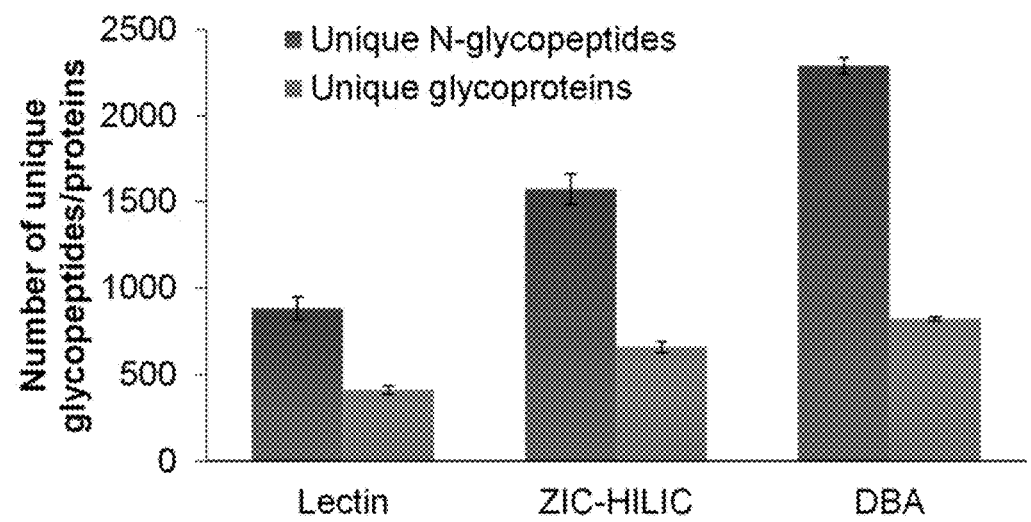

To test the effectiveness of the Dendrimer-conjugated Boronic Acid derivative (DBA) enrichment, triplicate parallel experiments were performed to compare the current method with the known lectin (combining wheat germ agglutinin (WGA) and concanavalin A (ConA)) and zwitterionic hydrophilic interaction liquid chromatography (ZIC-HILIC) enrichment methods. Each experiment started from the same amount of peptides from an MCF7 cell whole lysate (FIG. 3). For these parallel experiments, except the enrichment method, every other step was kept the same. Prior to this comparison, a comparison of 0.1% and 1% trifluoroacetic acid (TFA) as ion-pairing reagent for the ZIC-HILIC experiment and found that 1% TFA had slightly better performance (FIG. 3a). Therefore, 1% TFA was used in the comparison experiment. From the parallel experiments, the greatest number of unique N-glycopeptides were identified using the current DBA method, and more unique N-glycopeptides were identified with ZIC-HILIC than the lectin-based method (FIG. 3b).

Figure 3C:
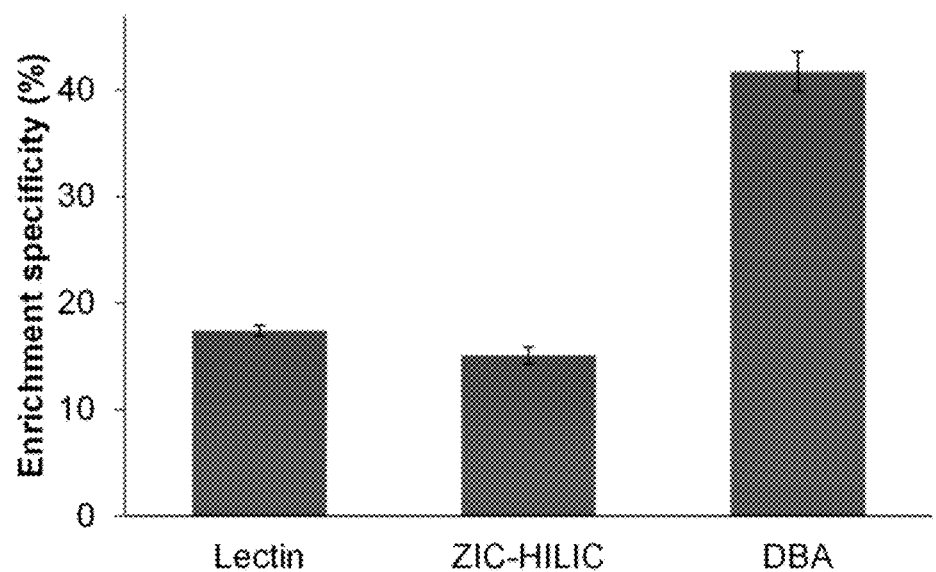

Regarding the specificity, the numbers of glycopeptides and non-glycopeptides identified in each of the parallel experiments was compared, and the results showed that the DBA method had the highest specificity (FIG. 3c). Without wishing to be bound by theory, it is thought that ZIC-HILIC allows for enrichment of a broader spectrum of glycopeptides than lectin, the principle of the ZIC-HILIC method is based on the hydrophilic property difference between glycopeptides and non-glycopeptides. Therefore, some hydrophilic but non-glycosylated peptides can also be enriched, lowering the enrichment specificity. Based on the number of unique glycopeptides identified, DBA outperformed the other two methods, while ZIC-HILIC had better performance than lectin. Furthermore, the disclosed method also has the highest enrichment specificity.

Example 4—Global Characterization of Protein N-Glycosylation in Yeast

Figure 4A:
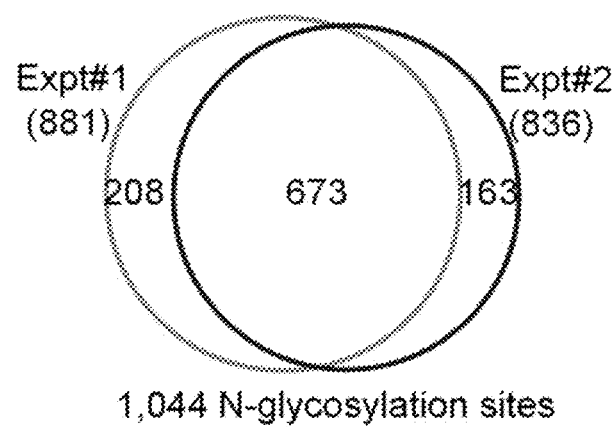
FIG. 4a-4f. Comprehensive analysis of protein N- and O-glycosylation in yeast.
Figure 15:
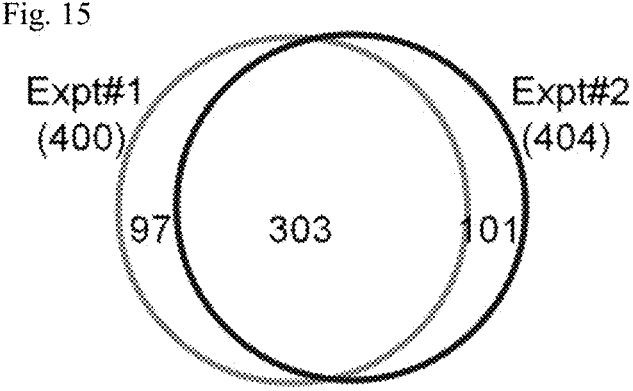
FIG. 15. Comparison of N-glycoproteins identified in yeast cells in duplicate experiments. A number of N-glycoproteins were identified in yeast using methods described herein.

Using the disclosed methods, biological duplicate experiments were performed for the global analysis of protein N- and O-glycosylation in yeast. For N-glycoprotein analysis, 881 sites on 400 proteins identified in one experiment and 836 sites on 404 proteins in another. Overall, 1,044 N-glycosylation sites (FIG. 4a) on 501 proteins (FIG. 15) were identified. To ensure that the sites were confidently identified, very stringent criteria were applied during analysis. First, the false positive rate at the N-glycopeptide level was well-controlled under 1.0%, based on the target-decoy method. Additionally, all N-glycosylation sites were required to contain the motif NX[S/T/C], where X is any amino acid except proline. The N-glycosylation site was also required to contain heavy oxygen ($^{18}O$) as a tag. To minimize possible spontaneous deamidation during PNGase F treatment in heavy-oxygen water, the reaction was run for only three hours. It is known that within three hours under mild conditions, spontaneous asparagine deamidation is negligible.

Figure 4B:
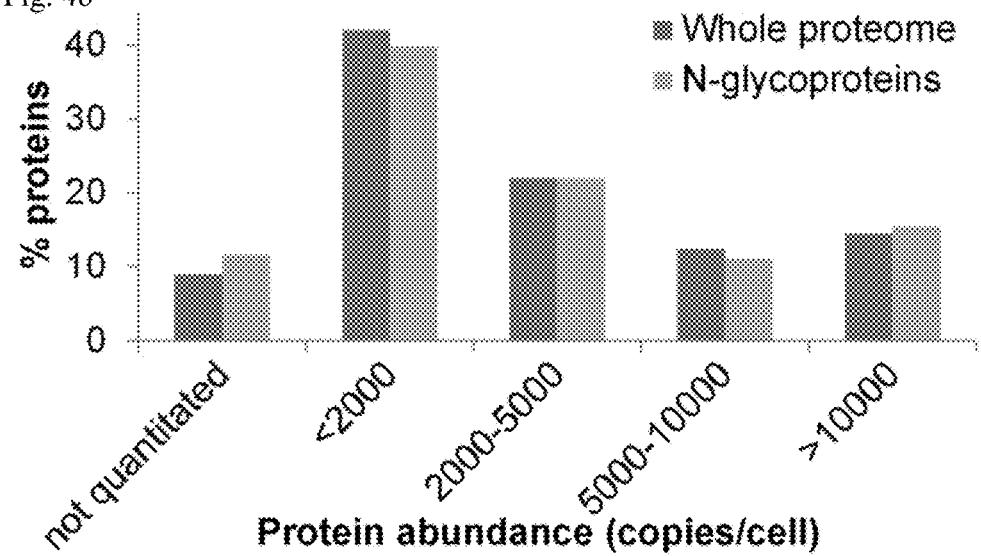
Figure 16:
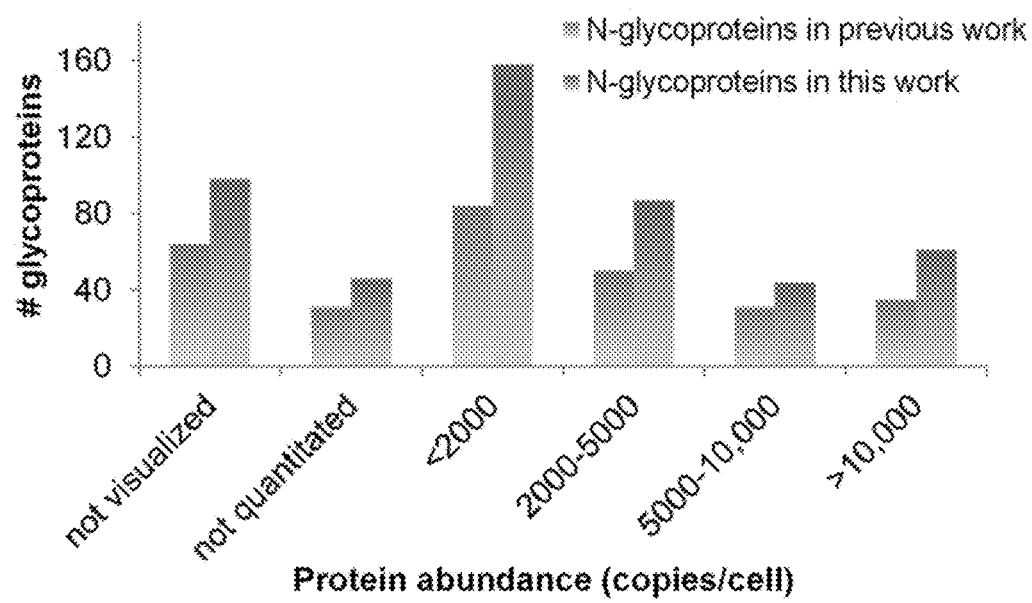
FIG. 16. Comparison of the abundance distributions of yeast N-glycoproteins identified in this work (right bars) and identified previously with the phenylboronic acid beads (left bars). More N-glycoproteins were identified in each bin with the disclosed method, especially for low-abundance N-glycoproteins.
Figure 17A:
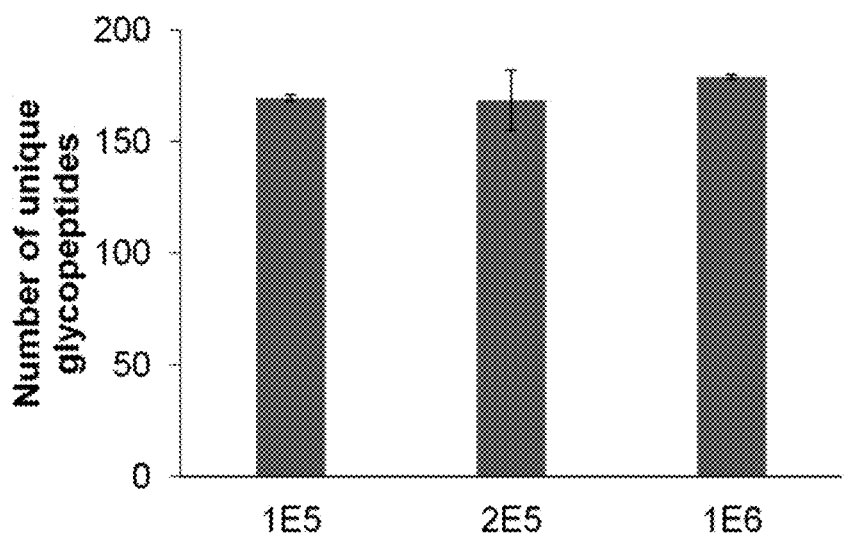
FIG. 17a-17e. MS parameters were optimized for yeast intact O-glycopeptide analysis using the Orbitrap cell to record tandem mass spectra of glycopeptides.
Figure 17B:
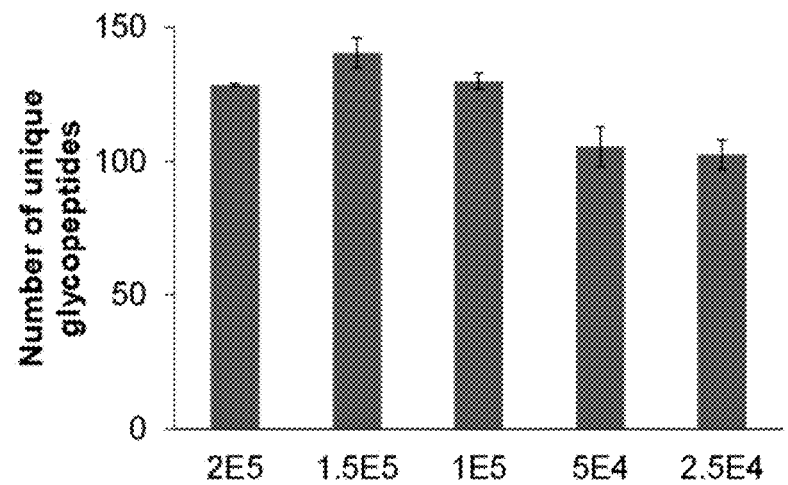
Figure 17C:
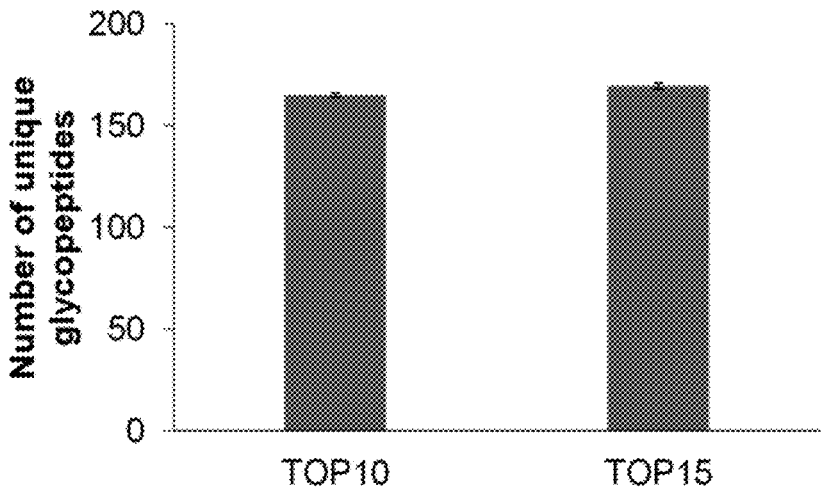
Figure 17D:
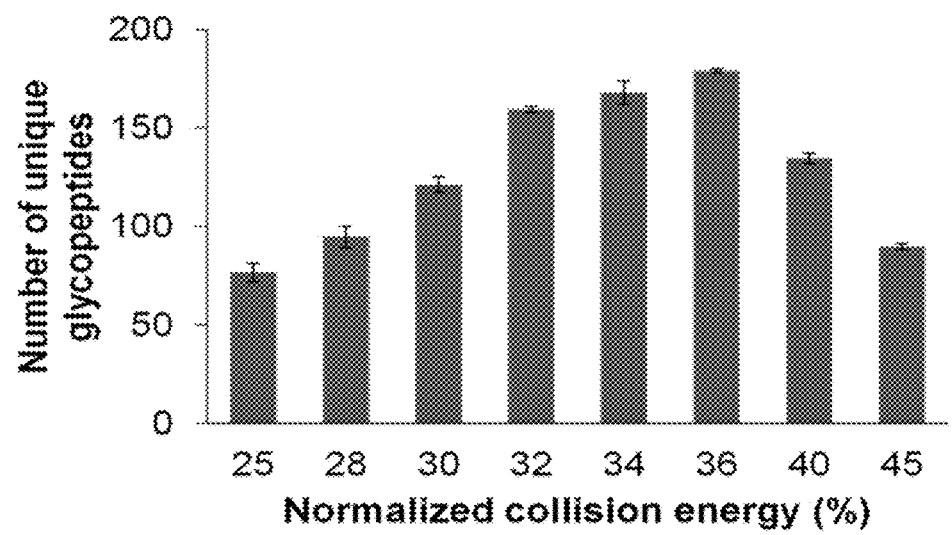
Figure 17E:
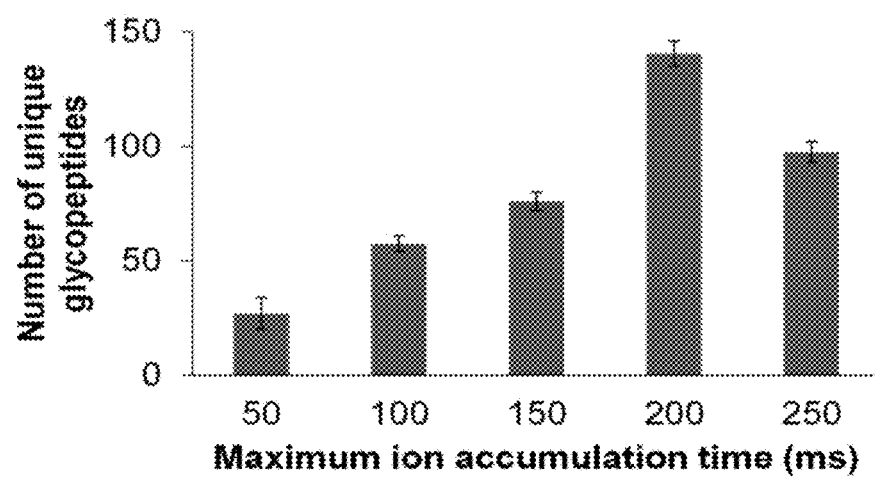

In order to demonstrate that low-abundance glycoproteins can be identified with the current method, the abundance distributions of identified N-glycoproteins and all proteins in the whole yeast proteome were compared, and they were very similar (FIG. 4b). Phenylboronic acid magnetic beads in yeast were also with the same criteria as above, and 716 N-glycosylation sites on 297 proteins were identified. The abundance distributions for both datasets are shown in FIG. 16. More N-glycoproteins were identified in each bin with the disclosed method, especially for low-abundance N-glycoproteins. For example, for proteins with abundances less than 2,000 copies per cell, about twice as many N-glycoproteins were identified using the disclosed methods (158 vs. 84), which demonstrated that the disclosed method is more effective in enriching low-abundance glycopeptides due to strengthened interactions from the BA derivative and synergistic interactions of DBA.

Example 5—Analyzing Protein O-Mannosylation in Yeast

The reversible covalent interactions can leave enriched glycopeptides with intact glycans for site identification and glycan structure elucidation. In baker's yeast, O-glycans consist of only mannose, but the number of mannose per glycan varies. The disclosed enrichment method can also enable global analysis of O-glycoproteins. In order to increase the identification confidence of intact O-glycopeptides, high-energy collisional dissociation (HCD) was employed for glycopeptide fragmentation, and the tandem mass spectra were recorded in the Orbitrap cell. Several important machine parameters, such as automatic gain control (AGC) target for MS and $MS^2$, normalized collision energy, and maximum ion accumulation time for $MS^2$, were optimized (FIG. 17). Byonic™ was used to search the raw files for the identification of protein O-mannosylation.

Several examples of the O-mannosylated peptides with different glycans were identified. 987 unique O-glycopeptides from 206 proteins were identified in the first experiment and 971 unique O-glycopeptides from 196 proteins in the second experiments. In total, 234 O-glycoproteins were identified, and 168 proteins were identified in both experiments. The overlap was very high (81.5 and 85.7%), which further demonstrated that the identification of glycopeptides and glycoproteins were highly confident. The current results show that the glycopeptide enrichment based on the reversible covalent interactions can keep enriched glycopeptides intact for site identification and glycan structure elucidation.

Figure 4C:
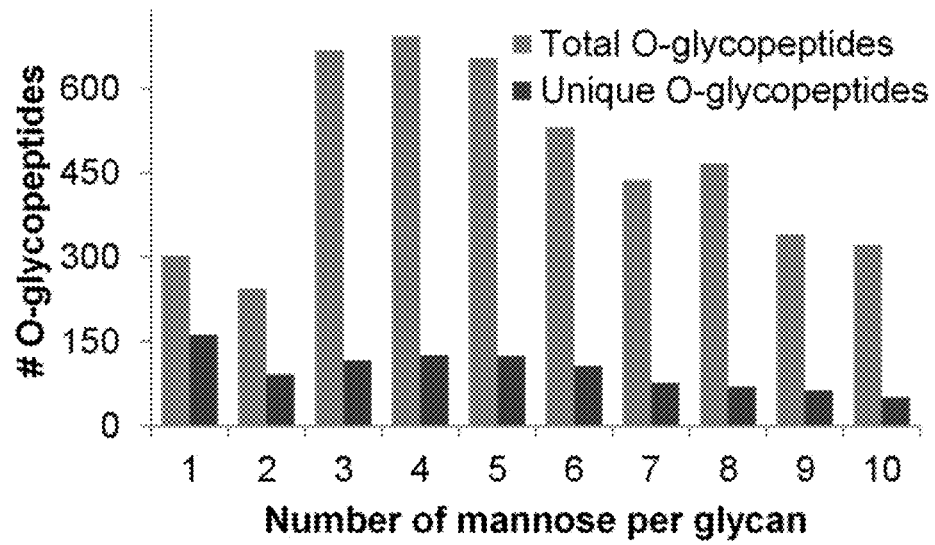
Figure 4D:
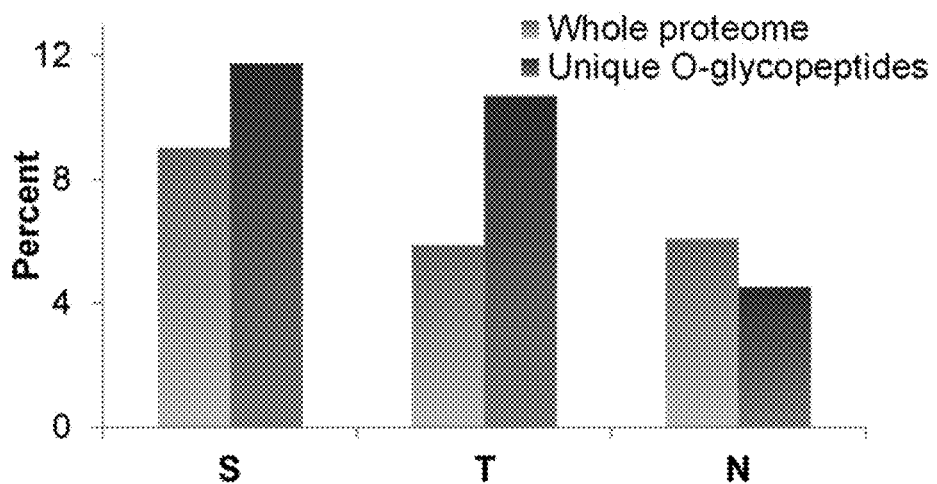

The distribution of the number of mannose per glycan is in FIG. 4c. The number of unique glycopeptides with one mannose is the highest, and the second are those with four mannoses. For glycopeptides with glycans containing more than four mannoses, the number decreases with the increasing number of mannoses. The site localization confidence is lower than that of N-glycosylation due to the neutral loss of O-glycans and the presence of many serine and threonine residues on O-glycopeptides (FIG. 4d). Compared to the whole yeast proteome, both S and T were more frequent in the identified unique O-glycopeptides, and the occurrence of T was almost two times as many (9.0 vs. 11.8% for S and 5.9 vs. 10.7% for T). Conversely, the frequency of N (N-glycosylation sites) in the identified O-glycopeptides was lower than the whole proteome (6.1 vs. 4.5%).

Figure 4E:
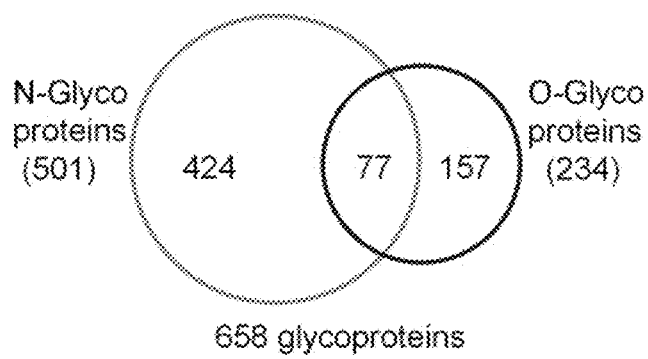
Figure 4F:
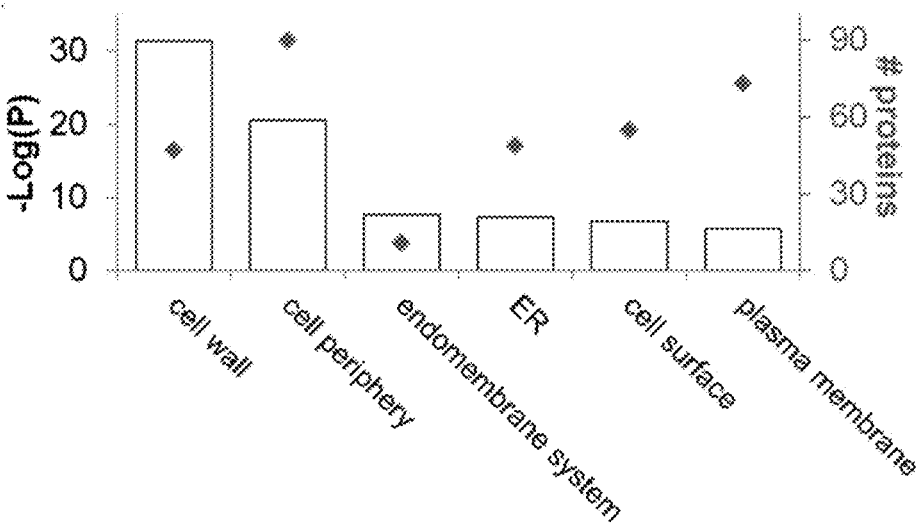
Figure 18:
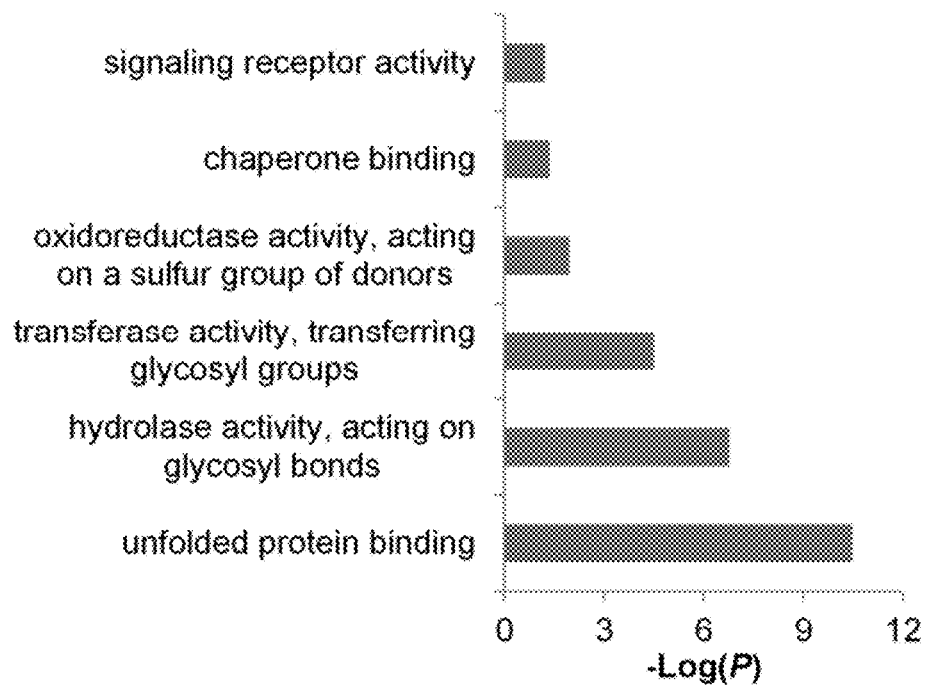
FIG. 18. Clustering of identified O-glycoproteins in yeast based on molecular function. P values were calculated using a modified Fisher's exact test.

In total, 234 O-glycoproteins were identified, and about one third were also N-glycosylated (FIG. 4e). O-glycoproteins located on the cell wall (P=4.25E-32, modified Fisher's exact test, which is also used for all other P value calculations except stated otherwise) are the most highly enriched when clustered using the Database for Annotation, Visualization and Integrated Discovery (DAVID) (FIG. 4f). Seventy-three O-glycoproteins belong to the endomembrane system, and 55 are located in the ER. Clustering of O-glycoproteins based on molecular function indicates that proteins related to hydrolase activity (acting on glycosyl bonds) and transferase activity (transferring glycosyl groups) are most highly enriched (FIG. 18). Based on reversible covalent interactions between DBA and glycans, protein O-glycosylation can be confidently identified, including valuable glycan structural information.

Example 6—Global Analysis of Protein N-Glycosylation in Human Cells

Figure 5A:
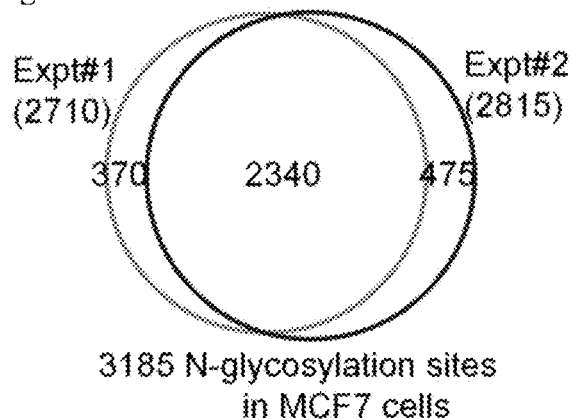
FIG. 5a-5g. Comprehensive analysis of protein N-glycosylation in human cells.

Due to the diversity of glycan structures, it is more challenging to globally analyze glycoproteins in human cells. The DBA method was applied to comprehensively analyze protein N-glycosylation in different types of human cells. Biological duplicate experiments were performed for MCF7 cells, and the number of glycosylation sites and glycoproteins identified in each experiment is shown in FIG. 5a and FIG. 19. With the well-controlled false discovery rate (FDR) of <1.0% at the glycopeptide level and stringent criteria described above, 2,710 N-glycosylation sites on 1,127 proteins were identified in one experiment, and 2,815 sites on 1,156 proteins in another. Overall, 2,340 common sites were identified in both experiments, which represent 86.3% and 83.1% of the total sites identified from each experiment, respectively. The overlap at the glycoprotein level was even higher: 981 common glycoproteins were identified. A total of 3,185 glycosylation sites were identified on 1,302 proteins in MCF7 cells.

The method was also employed to globally analyze protein N-glycosylation in HEK 293T and Jurkat cells; 3,052 sites were identified on 1,301 proteins in HEK 293T cells, and 2,120 sites on 948 proteins were found in Jurkat cells.

Figure 5B:
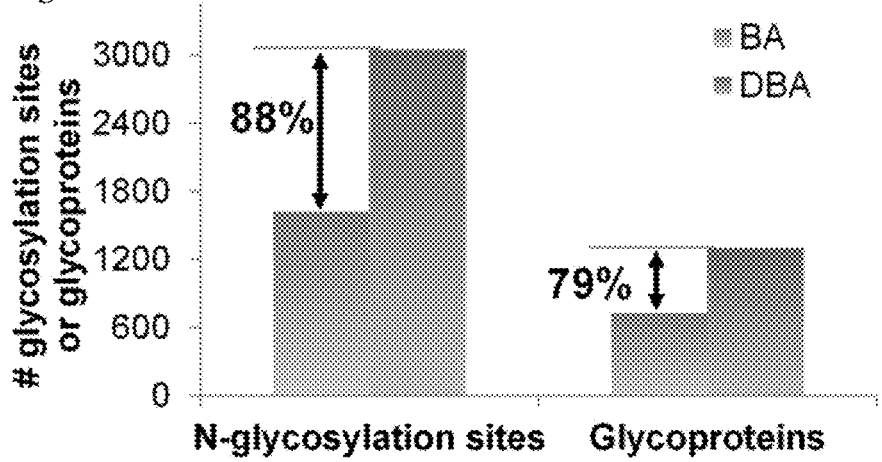
Figure 5C:
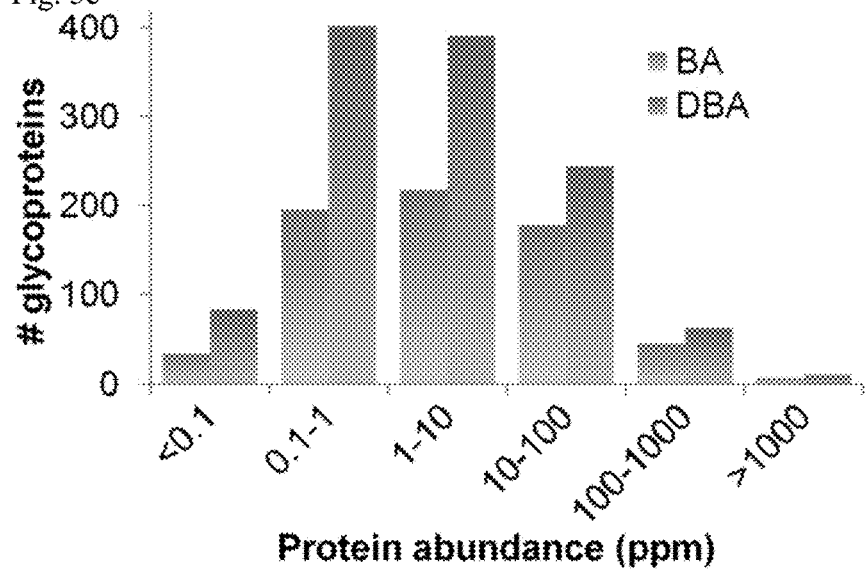

The effect of the dendrimer on glycopeptide enrichment was further investigated by comparing DBA vs. benzoboroxole (Formula II) conjugated magnetic beads without the dendrimer (designated as BA beads). With the DBA beads, 88% more N-glycosylation sites and 79% more glycoproteins were identified compared to the BA beads (FIG. 5b). The abundance distributions of all glycoproteins identified using either the DBA or BA beads are displayed in FIG. 5c (abundances from an online database (PaxDb)). The number of glycoproteins identified using the DBA beads was higher than that with the BA beads in each abundance category and the DBA method was especially superior for glycoproteins with very low abundance (less than 10 ppm). For low-abundance proteins, over twice as many N-glycoproteins were identified with the DBA beads (84 vs. 34 glycoproteins for <0.1 ppm, and 402 vs. 196 for 0.1-1.0 ppm). These results explicitly demonstrate that the synergistic interactions between multiple BA derivative molecules and glycans can greatly increase the coverage of low-abundance glycopeptides.

Figure 5D:
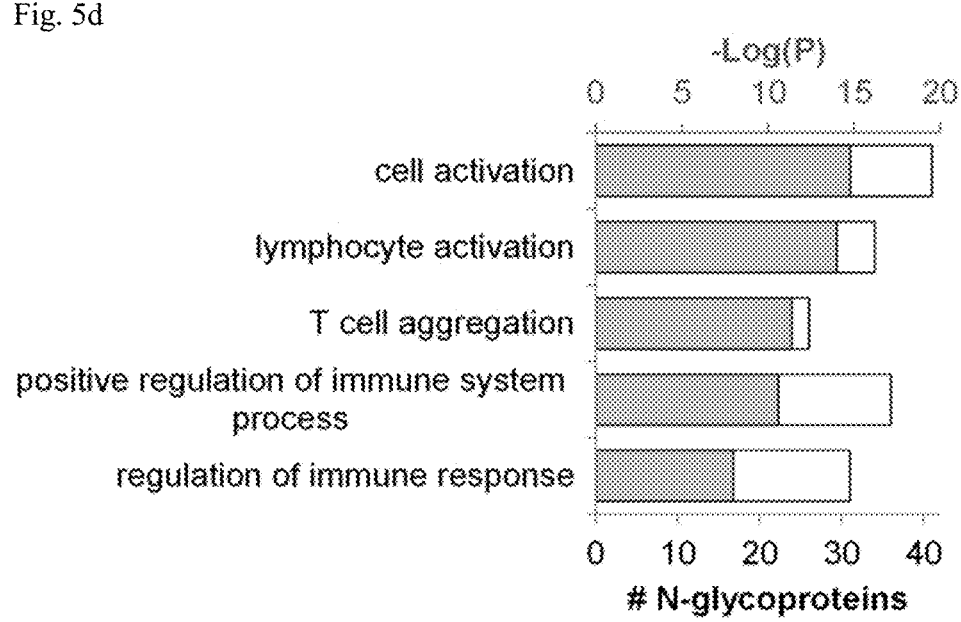
Figure 20:
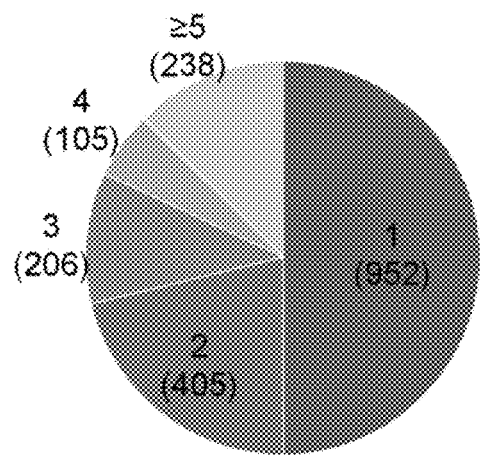
FIG. 20. The distribution of unique N-glycosylation sites per glycoprotein in human cells. Many proteins were shown to be glycosylated and to contain multiple unique glycosylation sites.

Combining the results from the three human cell lines, a total of 4,691 N-glycosylation sites on 1,906 proteins were identified. More than 10% of proteins (238) are highly glycosylated and contain at least five sites (FIG. 20). In consideration of different cell types, there is good overlap among identified N-glycoproteins in human cell experiments. One example highlighting differences between cell types are the N-glycoproteins (180) identified only in Jurkat cells, many of which are related to immune cell-specific activities, such as cell activation and cell immune response (FIG. 5d).

Figure 21A:
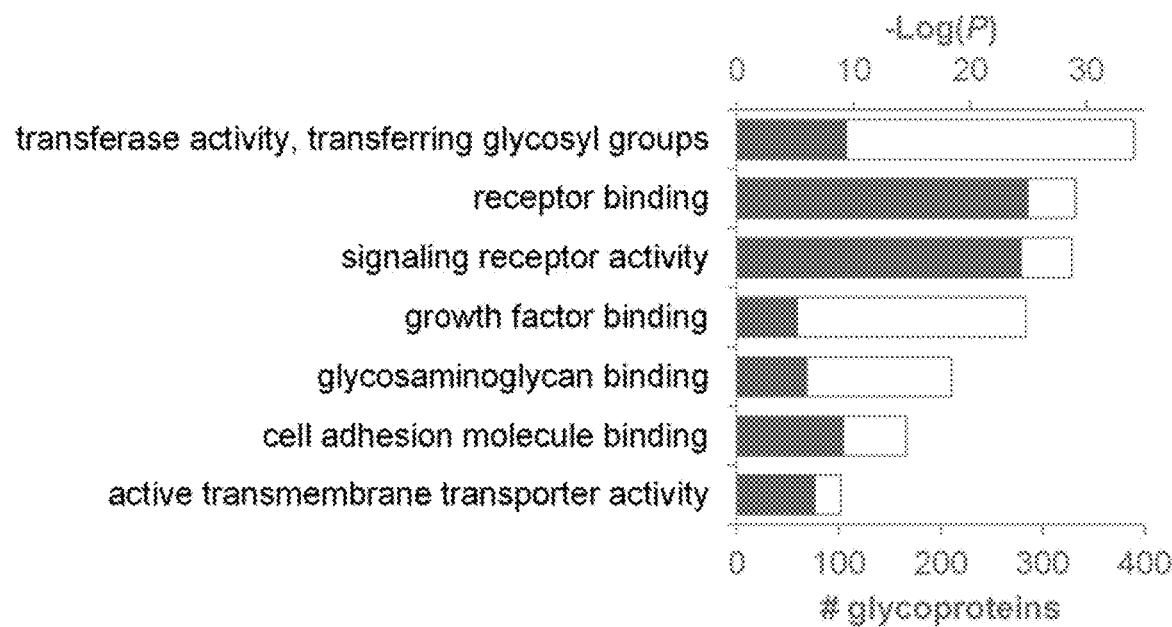
FIG. 21a-21b. Clustering of N-glycoproteins. Clustering is based on (FIG. 21a) molecular function and (FIG. 21b) cellular compartment. P values were calculated using a modified Fisher's exact test.

By clustering 1,906 N-glycoproteins according to molecular function, proteins related to glycosyl-transferase activity are the most highly enriched with a P value of 8.5E-35 (FIG. 21a), and 108 N-glycoproteins belong to this category. In yeast, this group of proteins is the second most highly enriched. The following groups of N-glycoproteins are also highly enriched in human cells: receptor binding, signaling receptor activity, growth factor binding proteins, glycosaminoglycan binding, cell adhesion molecule binding, and active transmembrane transporter activity.

Figure 5E:
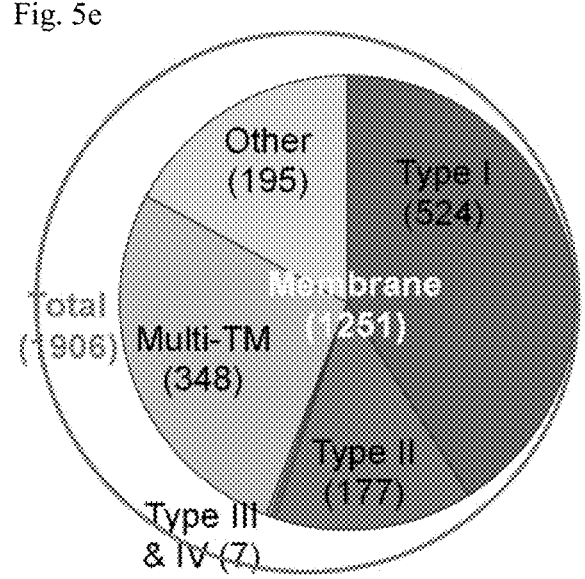
Figure 5F:
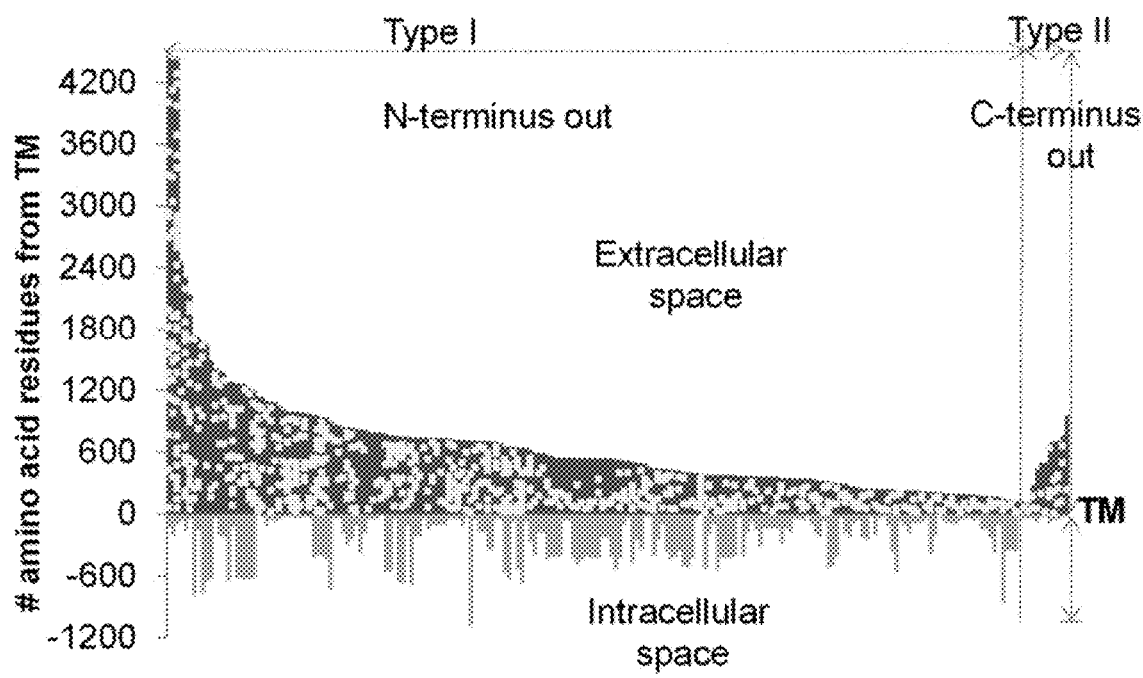
Figure 21B:
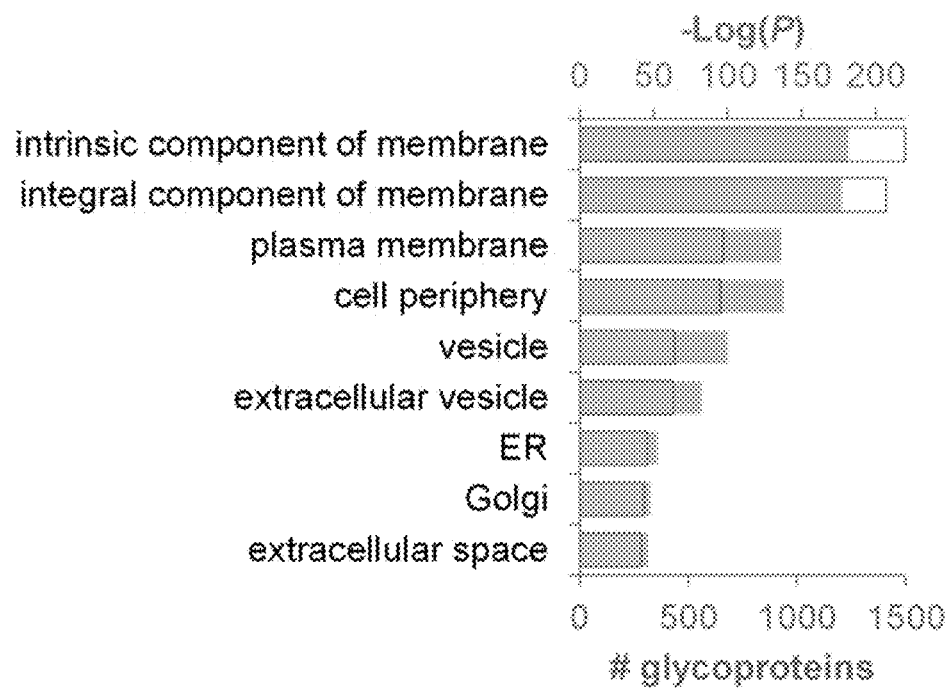

Many glycoproteins are known to be membrane proteins. Here, 1,251 out of 1,906 N-glycoproteins are membrane proteins, which are highly enriched with an extremely low P value of 1.6E-192. Glycoproteins in the cell periphery, vesicle, ER, Golgi, and extracellular space are all enriched with very low P values (FIG. 21b). Based on the information available on UniProt (uniprot.org), 524 of identified membrane proteins are type I membrane proteins, 177 are type II, and 348 proteins contain multiple transmembrane domains (FIG. 5e). A total of 301 receptors were identified among these N-glycoproteins; glycosylation site locations for receptors identified as type I and II membrane proteins are shown in FIG. 5f. All sites (1,079 sites) were located in the extracellular space, which corresponds very well with the belief that glycans are located on the extracellular side of surface membrane proteins.

Figure 5G:
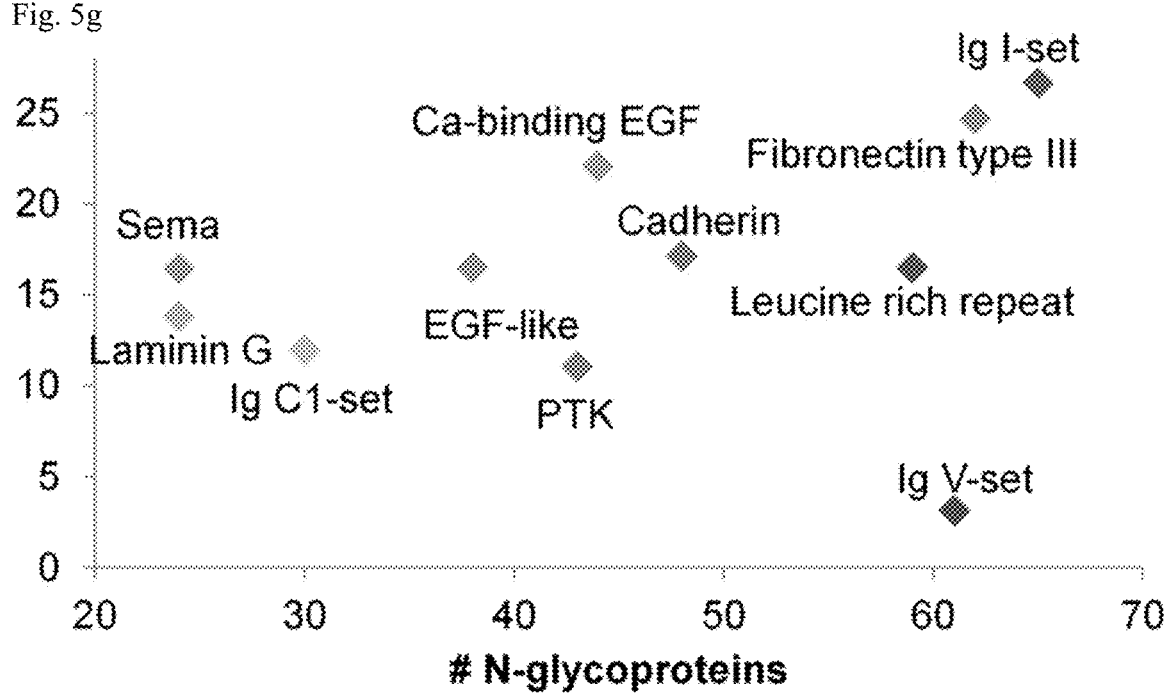

Domain analysis shows that many N-glycoproteins contain different types of Ig domains (such as I-set, V-set and C1-set). Besides Ig domains, other domains related to cell-cell adhesion are also highly enriched, including fibronectin type III, cadherin and laminin G (FIG. 5g). Domains corresponding with receptor activities, such as PTK (protein tyrosine kinase) and EGF (epidermal growth factor)-like domains, are also highly enriched.

Example 7—Analysis of Protein N-Glycosylation in Mouse Brain Tissues

The disclosed methods were further applied to analyze protein N-glycosylation in mouse brain tissues, and biological duplicate experiments were performed. After protein extraction and digestion, glycopeptides were enriched using the DBA beads, and enriched glycopeptides were fractionated, followed by analysis with an online LC-MS system.

Figure 22A:
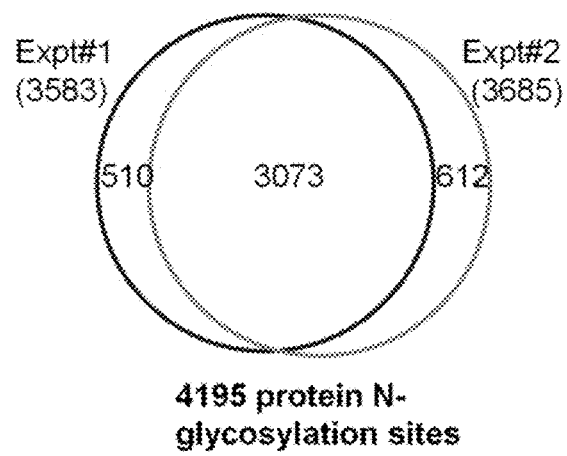
FIG. 22a-22b. Glycosylation sites in murine brain tissues. The number of protein N-glycosylation sites (FIG. 22a) and glycoproteins (FIG. 22b) identified in mouse brain tissues from biological duplicate experiments.
Figure 22B:
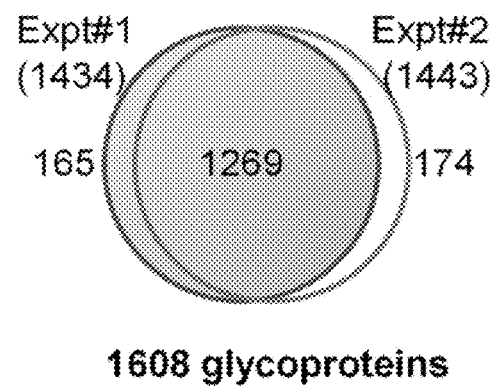

In the first experiment, we identified 3,583 sites on 1,434 glycoproteins, and very similar results were obtained in the second experiment (3,685 sites on 1,443 proteins). In total, 4,195 sites were identified on 1,608 proteins, and 3,073 common sites and 1,269 glycoproteins were found in both experiments, as shown in FIG. 22. Considering the large-scale analysis and the experiments being biologically duplicate, the overlap is very high at both the site (85.8 and 83.4% compared to the both experimental results, respectively) and protein (88.5 and 88.0%) levels, which is consistent with the above results from the duplicate experiments in human cells (Example 6). The highly reproducible results further demonstrate that the disclosed methods are effective.

Figure 23:
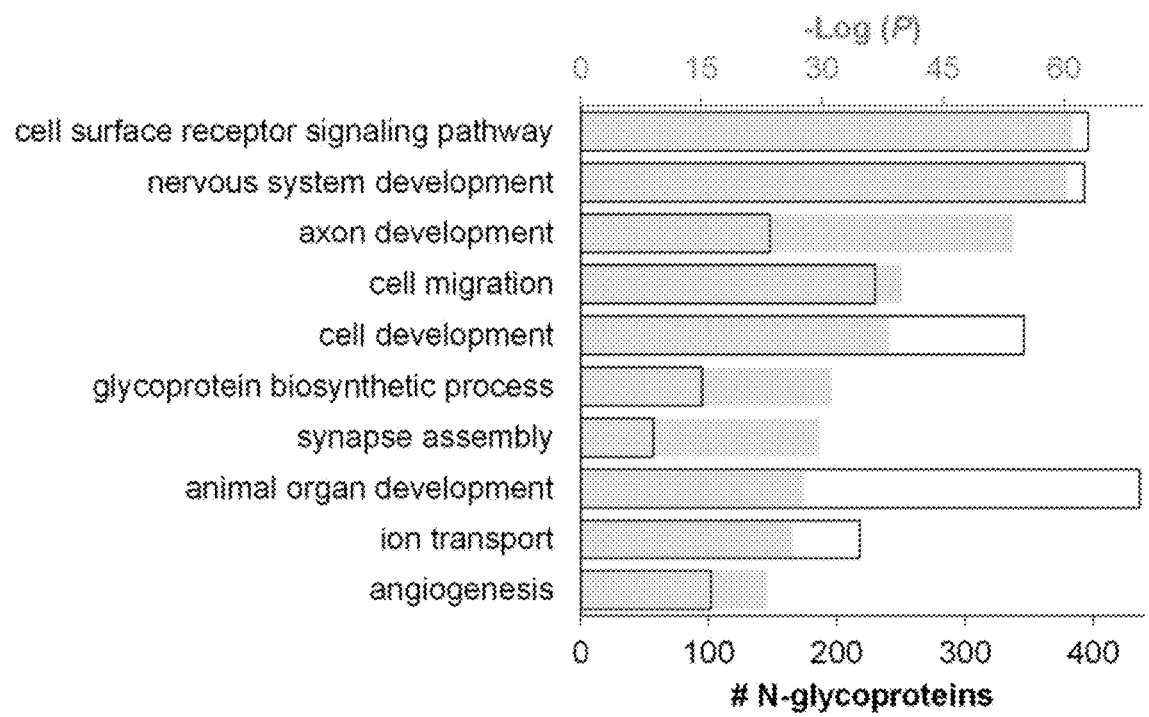
FIG. 23. Clustering of glycoproteins identified in mouse brain tissues based on biological process. P values were calculated using a modified Fisher's exact test.

Glycoproteins identified in the mouse brain tissues were clustered using DAVID based on biological process. About one quarter of identified glycoproteins (396) are related to cell surface receptor signaling pathway, which is the most highly enriched with a P value of 1.1E-61. Proteins related to brain-specific functions such as nervous system development (P=4.1E-61), axon development (P=1.9E-54), and synapse assembly (P=2.6E-30) were also highly enriched, as shown in FIG. 23. P values are calculated by a modified Fisher's exact test.

Figure 6A:
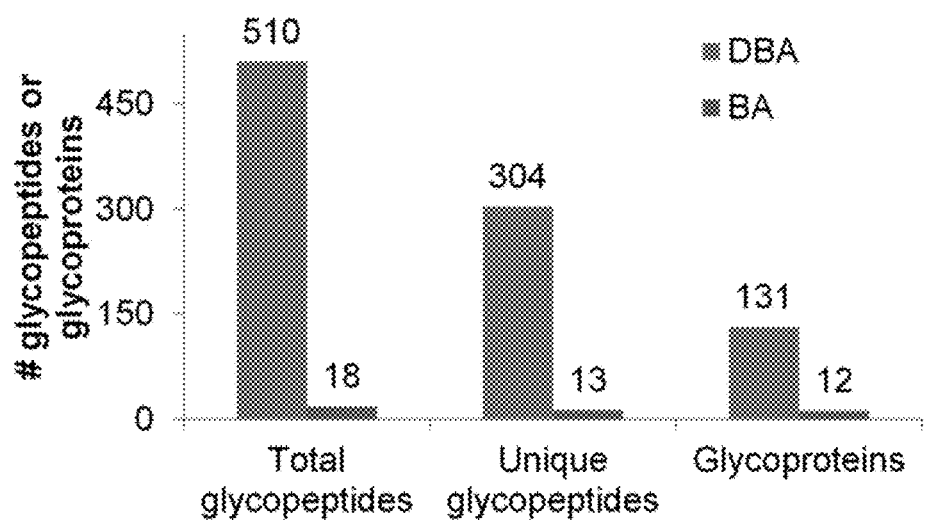
FIG. 6a-6d. The synergistic interactions dramatically enhanced the enrichment of O-GlcNAcylated peptides.
Figure 6B:
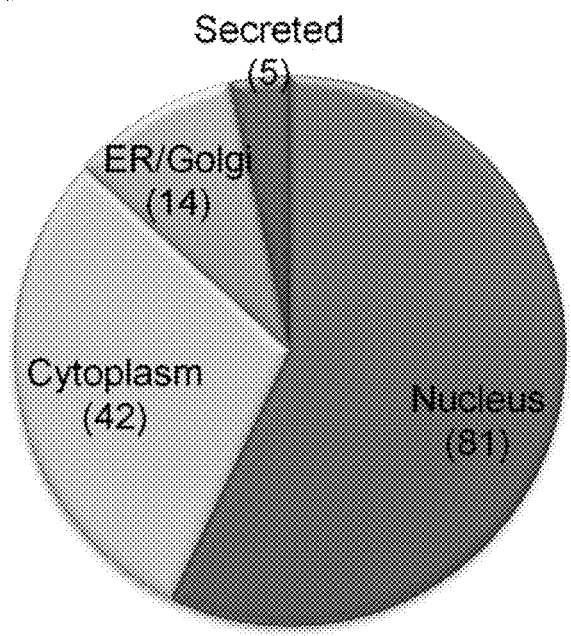
Figure 6C:
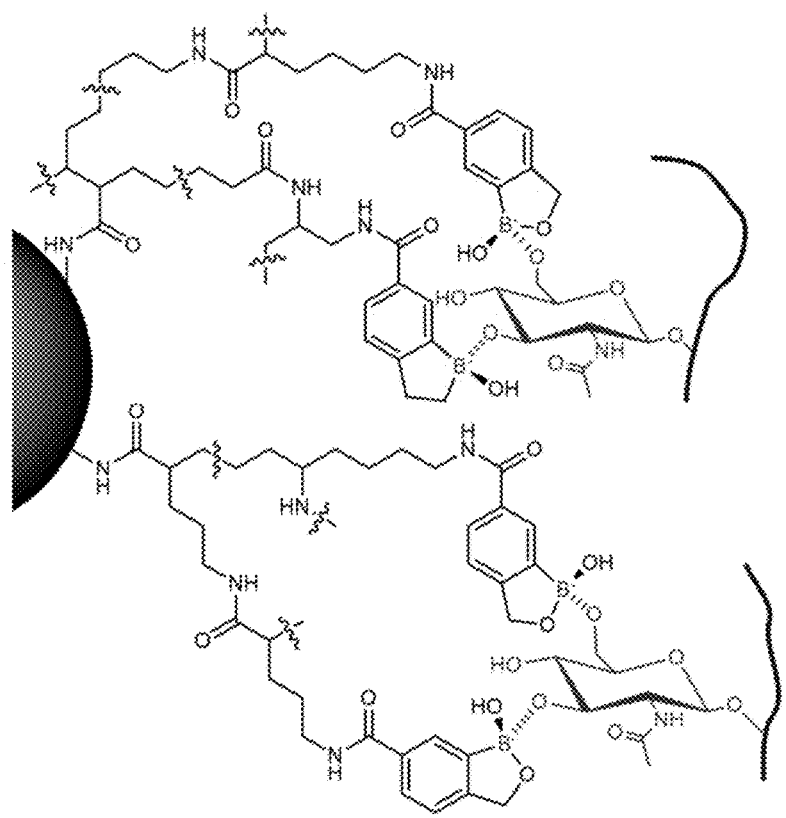

Example 8—Synergistic Interactions to Identify Protein O-GlcNAcylation 510 total glycopeptides with N-acetylhexosamine (HexNAc) (1) and 304 unique glycopeptides located on 131 proteins in HEK 293T cells were identified with the DBA enrichment (FIG. 6a). The BA derivative magnetic beads, only 18 total glycopeptides with HexNAc and 13 unique glycopeptides were found on 12 proteins. Among 131 glycoproteins, 81 were located in the nucleus (FIG. 6b), and typically, these proteins are O-GlcNAcylated because only glycoproteins with O-GlcNAc have been reported in the nucleus. Similarly, 131 O-glycoproteins with HexNAc(1) were identified in MCF7 cells, and 119 O-glycoproteins were found in Jurkat cells.

Figure 6D:
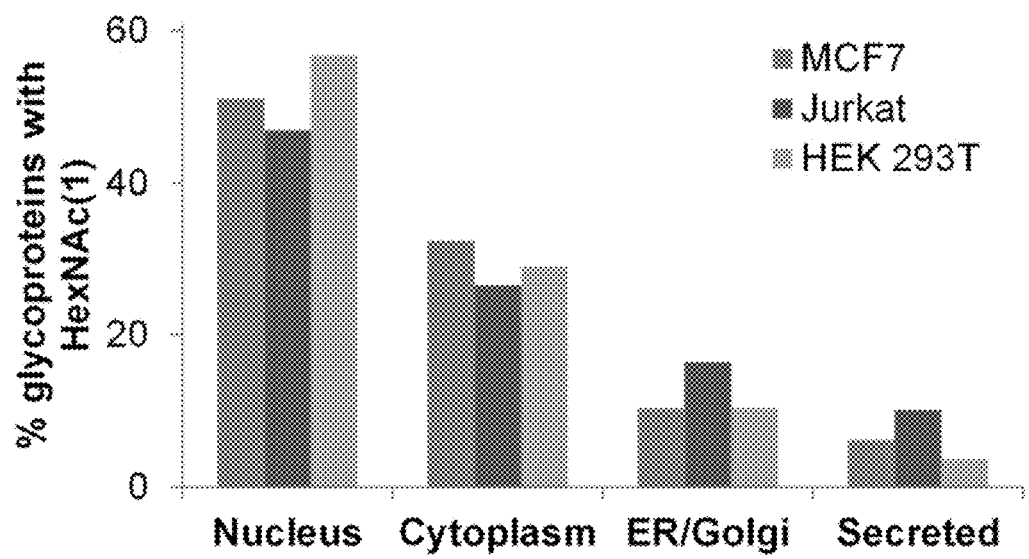

The effective enrichment of O-GlcNAcylated peptides may be attributed to the synergistic interactions with DBA beads. As discussed above, multiple sugars from one glycan synergistically interact with different benzoboroxle molecules on a single dendrimer bead. Although there is no cis-1,2-diol in GlcNAc, multiple hydroxyl groups in each GlcNAc may form reversible covalent bonds with several benzoboroxle molecules on a dendrimer bead, as shown in FIG. 6c. The synergistic interactions can dramatically facilitate the enrichment of O-GlcNAcylated peptides with DBA. The results are highly reproducible in different types of human cells (HEK 293T, MCF7 and Jurkat), for example, in glycoproteins with one HexNAc. The greatest number of identified glycoproteins (about 50%) are located in the nucleus of each cell type (FIG. 6d), and about 30% of them are in the cytoplasm. Glycoproteins in the nucleus and the cytoplasm are normally O-GlcNAcylated. In addition, ~12% of them are in the ER/Golgi. Only a small portion of glycoproteins (~7%) are secreted proteins, which are likely O-GalNAcylated.

Example 9—Cluster of Differentiation (CD) Molecules Identification

Figure 24A:
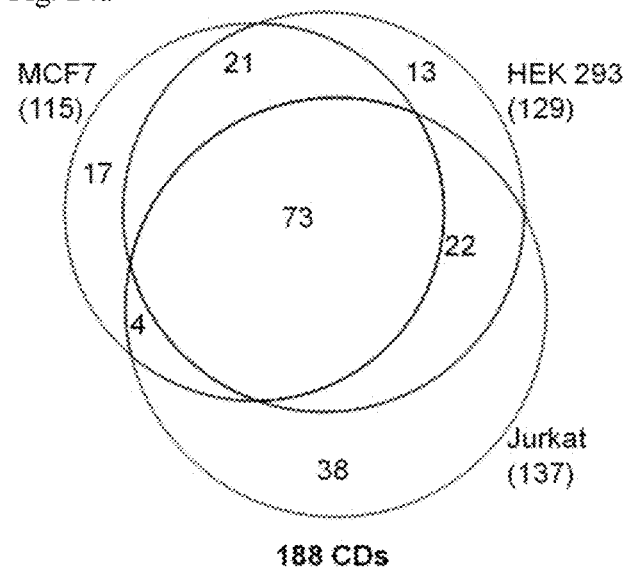
FIG. 24a-24b. CD N-glycoproteins identified in three types of human cells. The numbers of CD N-glycoproteins (FIG. 24a), and the percentage of CD glycoproteins with respect to all N-glycoproteins (FIG. 24b) identified in each type of human cells.
Figure 24B:
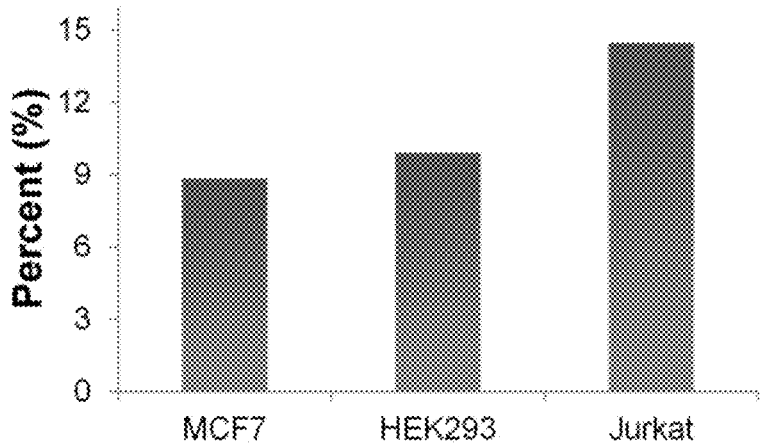
Figure 25:
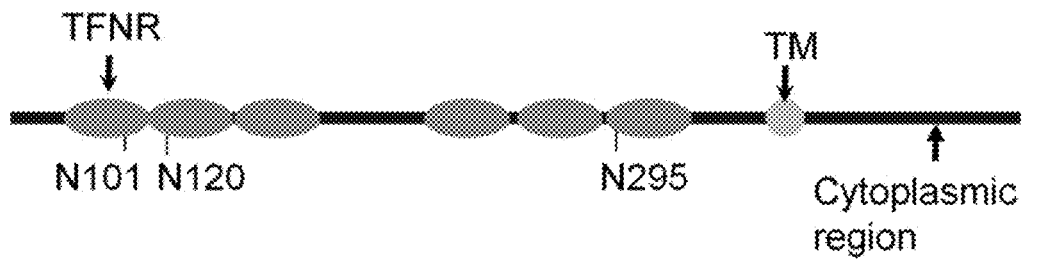
FIG. 25. Exemplary glycoproteins. Two examples of glycoproteins (CD30 and CD96) with domain and glycosylation site information in Jurkat cells.
Figure 25:
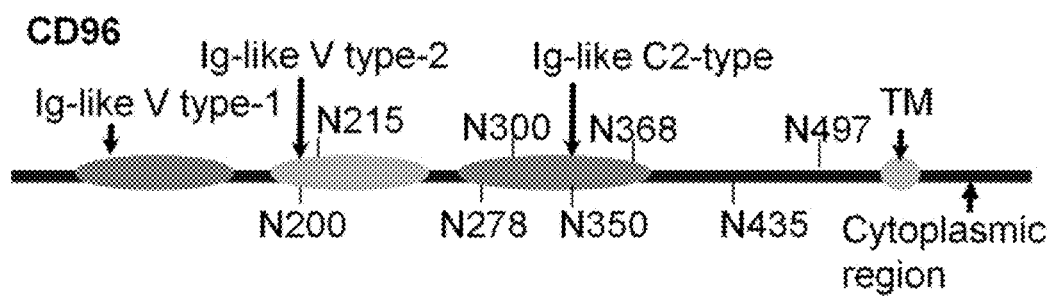

Cluster of differentiation (CD) molecules are those located on the cell surface that provide immunophenotyping targets for cell classification. In our experiment, 188 CD proteins were identified as N-glycoproteins. There were more CDs identified in Jurkat cells (137) than MCF7 (115) or HEK 293T (129) cells (FIG. 24a and FIG. 24b), despite the fact that the total N-glycoproteins identified in Jurkat cells were fewer. However, this result is consistent with the fact that more CDs are relevant to immune-related cells, including Jurkat cells. Two examples of glycoproteins identified in Jurkat cells are shown in FIG. 25, and the majority of identified N-glycosylation sites are located in extracellular domains. CDs with site-specific information may be more meaningful for cell classification and serve as effective biomarkers for disease detection.

Two examples of glycoproteins identified in Jurkat cells are shown in FIG. 25. TNFRSF8, also called CD30, is a receptor for TNFSF8/CD30L and may play a role in the regulation of cellular growth and transformation of activated lymphoblasts. Here, we identified three N-glycosylation sites (N101, N120 and N295), and all these sites were located in the TFNR domain, which is well-known to bind growth factors, and glycans on these domains may affect the binding. CD96 is T-cell surface protein tactile and may be involved in adhesive interactions of activated T and NK cells during the late phase of the immune response. It contains three Ig domains (Ig-like V type 1, Ig-like V type 2 and Ig-like C2-type). Six out of the eight N-glycosylation sites were identified in two domains, and all sites are located in the extracellular space. Glycosylation sites identified on CDs may carry more meaningful information for cell classification and serve as effective biomarkers for disease detection.

We claim:
1. A method for enriching a glycan-containing molecule, the glycan-containing molecule comprising a glycan component, the method comprising:
preparing a dendrimer-benzoboroxole (DB) complex comprising:
a benzoboroxole compound conjugated to a dendrimer; and
a bead;
contacting the glycan-containing molecule with the DB complex at pH 9-11 to form a glycan-DB complex;
wherein the glycan-containing molecule is reversibly bound to the DB complex; and
wherein the benzoboroxole compound is a compound of Formula II:

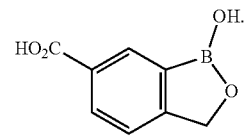

Formula (II)

.

2. The method of claim 1 further comprising:
washing the glycan-DB complex to remove non-glycan containing molecules from the glycan-DB complex.

3. The method of claim 1 further comprising:
releasing the glycan-containing molecule from the DB complex to form an enriched glycan-containing molecule;
wherein the releasing step is performed with an acid.

4. A composition comprising a dendrimer-benzoboroxole (DB) complex at pH 9 to 11 comprising:
a benzoboroxole compound of Formula II conjugated to a dendrimer;
a glycan-containing molecule covalently bound to the benzoboroxole compound; and
a bead,
wherein Formula II is:

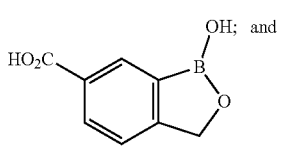

Formula (II)

wherein
the DB complex is configured to contact and enrich the glycan-containing molecule from a complex biological sample,
wherein the glycan-containing molecule is covalently bound to the DB complex under basic pH,
wherein the bead is configured to enable enrichment of the DB complex with the covalently bound glycan-containing molecule from the complex biological sample,
wherein the covalently bound glycan-containing molecule is released from the DB complex by an acid, and
wherein the released glycan-containing molecule is analyzed.

5. The composition of claim 4, wherein the bead is a magnetic bead.

6. The composition of claim 4, wherein a glycan component of the glycan-containing molecule is covalently bound to the benzoboroxole compound.

7. The composition of claim 4, wherein a plurality of benzoboroxole compounds are conjugated to a single dendrimer.

8. The composition of claim 7, wherein a glycan component of the glycan-containing molecule is covalently bound to the plurality of benzoboroxole compounds.

9. A method for analyzing glycosylation sites on a glycan-containing molecule, the glycan-containing molecule comprising at least one glycan component, the method comprising:
contacting the glycan-containing molecule with a dendrimer benzoboroxole (DB) complex at pH 9-11 to form a glycan-DB complex;
washing the glycan-DB complex to remove non-glycan-containing molecules from the glycan-DB complex;
releasing the glycan-containing molecule from the DB complex to form an enriched glycan-containing molecule;
cleaving the at least one glycan component from the enriched glycan-containing molecule; and
analyzing the at least one glycan component,
wherein the benzoboroxole is of Formula II:

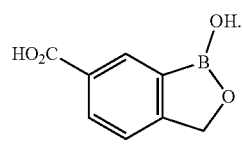

Formula (II)

10. The method of claim 9, wherein:
the releasing step is performed by an acid; and
the analyzing step is performed by mass spectrometry.

* * * * *